US006060037A

United States Patent [19]

Waldman

[11] Patent Number: 6,060,037
[45] Date of Patent: *May 9, 2000

[54] COMPOSITIONS THAT SPECIFICALLY BIND TO COLORECTAL CANCER CELLS AND METHODS OF USING THE SAME

[75] Inventor: Scott A. Waldman, Ardmore, Pa.

[73] Assignee: Thomas Jefferson University, Philadelphia, Pa.

[*] Notice: This patent is subject to a terminal disclaimer.

[21] Appl. No.: 08/635,930

[22] PCT Filed: Oct. 26, 1994

[86] PCT No.: PCT/US94/12232

§ 371 Date: Apr. 26, 1996

§ 102(e) Date: Apr. 26, 1996

[87] PCT Pub. No.: WO95/11694

PCT Pub. Date: May 4, 1995

Related U.S. Application Data

[63] Continuation-in-part of application No. 08/141,892, Oct. 26, 1993, Pat. No. 5,518,888, and a continuation-in-part of application No. 08/305,056, Sep. 13, 1994, Pat. No. 5,601,990.

[51] Int. Cl.$^7$ .......................... A61K 49/00; A61K 51/00; C12Q 1/68; C01N 33/566

[52] U.S. Cl. ...................... 424/1.65; 424/9.1; 424/143.1; 435/6; 435/7.23; 435/7.8; 435/92.1; 514/44; 536/24.31; 536/24.33

[58] Field of Search ................................. 435/6, 7.1, 7.2, 435/7.21, 7.23, 7.9, 325, 375, 92.1, 7.8; 514/13, 14, 44; 530/300, 326, 327; 536/23.1; 424/1.11, 1.65, 1.69, 9.1, 143.1

[56] References Cited

U.S. PATENT DOCUMENTS

| | | | |
|---|---|---|---|
| 4,584,268 | 4/1986 | Ceriani et al. | 436/504 |
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |
| 5,075,216 | 12/1991 | Innis et al. | 435/6 |
| 5,160,723 | 11/1992 | Welt et al. | 424/1.1 |
| 5,237,015 | 8/1993 | Garbers et al. | 530/350 |
| 5,237,051 | 8/1993 | Garbers et al. | 530/350 |
| 5,518,888 | 5/1996 | Waldman | 435/7.23 |
| 5,601,990 | 2/1997 | Waldman | 435/7.23 |
| 5,731,159 | 3/1998 | Waldman | 435/7.9 |
| 5,879,656 | 3/1999 | Waldman | 424/149 |

FOREIGN PATENT DOCUMENTS 839512 12/1983 South Africa.

OTHER PUBLICATIONS

Chelly, J. et al., "Illegitimate transcription: Transcription of any gene in any cell type", *Proc. Natl. Acad. Sci. USA,* 1989, 86, 2617–2621.

Chelly, J. et al., "Illegitimate Transcription: Application to the Analysis of Truncated Transcripts of the Dystrophin Gene in Nonmuscle Cultured Cells from Duchenne and Becker Patients", *J. Clin. Invest.,* 1991, 88(4), 1161–1166.

Cooper, D.N. et al., "Ectopic (Illegitimate) Transcription: New Possibilities for the Analysis and Diagnosis of Human Genetic Disease", *Ann. Med.,* 1994, 26(1), 9–14.

Kaplan, J.C. et al., "Illegitimate transcription: its use in the study of inherited disease", *Human Mutation,* 1992, 1(5), 357–360 (Abstract only).

Negrier, C. et al., "Illegitimate transcription: its use for studying genetic abnormalities in lymphoblastoid cells from patients with Glanzmann thrombasthenia", *British J. Haematology,* 1998, 100(1), 33–39.

Zippelius, A. et al., "Limitations of Reverse–Transcriptase Polymerase Chain Reaction Analyses for Detection of Micrometastatic Epithelial Cancer Cells in Bone Marrow", *J. Clin. Oncology,* 1997, 15(7), 2701–2708.

Aitken, R. et al., "Recombinant enterotoxins as vaccines against *Escherichia coli*–mediated diarrhoea", *Vaccine,* 1993, 11(2), 227–233.

Field, M., "Role of Cyclic Nucleotides in Enterotoxic Diarrhea", *Mol. Cyclic Nucl. Res.,* 1980, 12, 267–277.

Giannella, R.A., "Pathogenesis of Acute Bacterial Diarrheal Disorders", *Ann. Rev. Med.,* 1981, 32, 341–357.

Rao, M.C. et al., "Enterotoxins and Anti–toxins: Enterotoxins and ion transport", *Biochem.,* 1984, 12, 177–180.

Almenoff et al., "Ligand–based Histochemical Localization and Capture of Cells Expressing Heat–Stable Enterotoxin Receptors", *Molecular Microbiology 8:* 865–873 (1993).

Bjorn et al., "Antibody–Pseudomonas Exotoxin A Conjugates Cytotoxic to Human Breast Cancer Cells In Vitro", *Cancer Research 46:* 3262–3267 (1986).

Bjorn et al., "Evaluation of Monoclonal Antibodies for the Development of Breast Cancer Immunotoxins", *Cancer Research 45:* 1214–1221 (1985).

Bodansky et al., "Peptide Synthesis", John Wiley and Sons, 2d Ed. (1976).

Burgess et al., "Biological Evaluation of a Methanol–Soluble, Heat–Stable *Escherichia coli* Enterotoxin in Infant Mice, Pigs, Rabbits, and Calves", *Infection and Immunity 21:* 526–531 (1978).

(List continued on next page.)

*Primary Examiner*—John S. Brusca
*Assistant Examiner*—Thomas G. Larson
*Attorney, Agent, or Firm*—Woodcock Washburn Kurtz Mackiewicz & Norris LLP

[57] ABSTRACT

Conjugated compounds which comprise an ST receptor binding moiety and a radiostable active moiety are disclosed. Pharmaceutical compositions comprising conjugated compound which comprises an ST receptor binding moiety and a radiostable active moiety or an ST receptor binding moiety and a radioactive active moiety are disclosed. Methods of treating an individual suspected of suffering from metastasized colorectal cancer are disclosed. Methods of radioimaging metastasized colorectal cancer cells are disclosed. In vitro methods, kits and reagents are disclosed for determining whether or not an individual has metastasized colorectal cancer cells, for determining whether tumor cells are colorectal in origin and for analyzing tissue samples from the colon tissue to evaluate the extent of metastasis of colorectal tumor cells.

10 Claims, No Drawings

OTHER PUBLICATIONS

Cawley and Herschman, "Epidermal Growth Factor–Toxin A Chain Conjugates: EGF–Ricin A is a Potent Toxin While EGF–Diphtheria Fragment A is Nontoxic", *Cell 22:* 563–570 (1980).

Ceriani, R. et al., "Variability in Surface Antigen Expression of Human Breast Epithelial Cells Cultured from Normal Breast, Normal Tissue Peripheral to Breast Carcinomas, and Breast Carcinomas", *Cancer Res.* Jul. 1984, 44, 3033–3039.

Ceriani, R. et al., "Circulating Human Mammary Epithelial Antigens in Breast Cancer", *PNAS USA* 1982, 79, 5420–5424.

Chan and Giannella, "Amino Acid Sequence of Heat–stable Enterotoxin Produced by *Escherichia coli* Pathogenic for Man", *J. Biol. Chem. 256:* 7744–7746 (1981).

Chung and Collier, "Enzymatically Active Peptide from the Adenosine Diphosphate–Ribosylating Toxin of *pseudomonas Aeruginosa*" *Infection and Immunity 16:* 832–841 (1977).

Cohen, M. et al., "Receptors for *Escherichia coli* Heat Stable Enterotoxin in Human Intestine and in a Human Intestinal Cell Line (Caco-2)", *J. Of Cellular Physiol.* 1993, 156, 138–144.

Corstens, F. And van der Meer, Jos. W.M., "Chemotactic Peptides: New Locomotion for Imaging of Infection?", *J. Nucl. Med.* 1991, 32(3), 491–494.

Cumber et al., "Preparation of Antibody–Toxin Conjugates", *Methods in Enzymology 112:* 207–225 (1985).

Currie et al., "Guanylin: An Endogenous Activator of Intestinal Guanylate Cyclase", *Proc. Natl. Acad. Sci. USA 89:* 947–951 (1992).

de Sauvage, F. et al., "Primary Structure and Functional Expression of the Human receptor for *Escherichia coli* Heat–Stable Enterotoxin", *The J. of Biol. Chem.* 1991, 266, 17912–17918.

Drewett, J. And Garbergs, "The Family of Guanylyl Cyclase Receptors and Their Ligands", *Endocrine Reviews* 1994, 15(2), 135–162.

Dreyfus et al, "Chemical Properties of Heat–Stable Enterotoxins Produced by Enterotoxigenic *Escherichia Coli* of Different Host Origins", *Infection and Immunity 42:* 539–548 (1983).

Eckelman et al., "Comparison of $^{99m}$Tc and $^{111}$In Labeling of Conjugated Antibodies", *Nucl. Med. Biol. 13:* 335–343 (1986).

Evans et al., "Differences in the Response of Rabbit Small Intestine to Heat–Labile and Heat–Stable Enterotoxins of *Escherichia Coli*", *Infection and Immunity 7:* 873–880 (1973).

Forte, L. et al., "Receptors and cGMP Signalling Mechanism for *E. Coli* Enterotoxin in Opossum Kidney", *Am. J. Physiol.* Nov. 1988, 255 (5 Pt. 2), F1040–F1046.

Forte, L. et al., "*Escherichia coli* Enterotoxin Receptors: Localization in Opossum Kidney, Intestine, and Testis", *Am. J. Physiol.* Nov. 1989, 257 (5 Pt. 2), F874–881.

Fischmann, A.J. et al., "A Ticket to Ride: Peptide Radiopharmaceuticals", *J. Nucl. Med.* 1993, 34(12), 2253–2263.

Fitzgerald et al., "Adenovirus–Induced Release of Epidermal Growth Factor and Pseudomonas Toxin into the Cytosol of KB Cells during Receptor–Mediated Endocytosis", *Cell 32:* 607–617 (1983).

Fitzgerald, "Construction of Immunotoxins Using Pseudomonas Exotoxin A", *Methods in Enzymology 151:* 139–145 (1987).

Giannella et al., "Development of a Radioimmunoassay for *Escherichia coli* Heat–Stable Enterotoxin: Comparison with the Suckling Mouse Bioassay", *Infection and Immunity 33:* 186–192 (1981).

Gros et al., "Biochemical Aspects of Immunotoxin Preparation", *J. Immunol. Meth. 81:* 283–297 (1985).

Guarino, A. et al., "$T_{84}$ Cell Receptor Binding and Guanyl Cyclase Activation by *Escherichia coli* Heat–Stable Toxin", *Am. J. Physiol. 253* Gastrointest. Liver Physiol. 16): G775–780, 1987.

Guerrant, R. et al., "Activation of Intestinal Guanylate Cyclase by Heat–Stable Enterotoxin of *Escherichia coli:* Studies of Tissue Specificity, Potential Receptors, and Intermediates", *J. Infect. Dis.* Aug. 1980, 142(2), 220–228.

Gyles, C.L., "Discussion: Heat–Labile and Heat–Stable Forms of the Enterotoxin from *E. Coli* Strains Enteropathogenic For Pigs", *Ann N.Y. Acad. Sci. 16:* 314–321 (1979).

Hakki et al., "Solubilization and Characterization of Functionally Coupled *Escherichia Coli* Heat–Stable Toxin Receptors and Particulate Guanylate Cyclase Associated with the Cytoskeleton Compartment of Intestinal Membranes", *Int. J. Biochem 25:* 557–566 (1993).

Hardingham, J.E. et al., "Immunobead–PCR: A Technique for the Detection of Circulating Tumor Cells Using Immunomagnetic Beads and the Polymerase Chain Reaction", *Cancer Res.* Aug. 1, 1993, 53, 3455–3458.

Hugues et al., "Identification and Characterization of a New Family of High–Affinity Receptors for *Escherichia coli* Heat–Stable Enterotoxin in Rat Intestinal Membranes", *Biochemistry 30:* 10738–10745 (1991).

Humm, J.L. et al., "Dosimetric Aspects of Radiolabeled Antibodies for Tumor Therapy", *J. of Nuclear Medicine* 1986, 27, 1490–1497.

Klipstein et al., "Development of a Vaccine of Cross–Linked Heat–Stable and Heat–Labile Enterotoxins that Protects Against *Escherichia Coli* Producing Either Enterotoxin", *Infection and Immunity 37:* 550–557 (1982).

Krause, W. et al., "Autoradiographic Demonstration of Specific Binding Sites for *E. Coli* Enterotoxin in Various Epithelia of the North American Opossum", *Cell Tissue Res.* 1990, 260, 387–394.

Krejcarek and Tucker, "Covalent Attachment of Chelating Groups to Macromolecules", *Biochemical and Biophysical Research Communications 77:* 581–585 (1977).

Kwok, "Calculation of Radiation Doses for Nonuniformly Distributed β and γ Radionuclides in Soft Tissue", *Med. Phys. 12:* 405–412 (1985).

Leonard et al., "Kinetics of Protein Synthesis Inactivation in Human T–Lymphocytes by Selective Monoclonal Antibody–Ricin Conjugates", *Cancer Research 45:* 5263–5269 (1985).

Lima, A. et al., "The Effects of *Escherichia coli* Heat–Stable Enterotoxin in Renal Sodium Tubular Transport", *Pharmacology & Toxicology* 1992, 70, 163–167.

Magerstadt, M., *Antibody Conjugates and Malignant Disease* Boca Raton: CRC Press, pp. 42–45 and 110–152 (1991).

Masuho et al., "Importance of the Antigen–Binding Valency and the Nature of the Cross–Linking Bond in Ricin A–Chain Conjugates with Antibody", *J. Biochem 91:* 1583–1591 (1982).

Merrifield, "Solid Phase Peptide Synthesis. I. The Synthesis of a Tetrapeptide", *J. Am. Chem. Society 15:* 2149–2154 (1963).

Michel and Dirkx, "Fluorescence Studies of Nucleotides Binding to Diphtheria Toxin and Its Fragment A", *Biochimica et Biophysica Acta 365:* 15–27 (1974).

Moseley et al., "Isolation and Nucleotide Sequence Determination of a Gene Encoding a Heat–Stable Enterotoxin of *Escherichia Coli*", *Infection and Immunity 39:* 1167–1174 (1983).

Okamoto et al., "Substitutions of Cysteine Residues of *Escherichia Coli* Heat–Stable Enterotoxin By Oligonucleotide–Directed Mutagenesis", *Infection and Immunity 55:* 2121–2125 (1987).

Rao, M. et al., "Mode of Action of Heat–Stable *Escherichia coli* Enterotoxin Tissue and Subcellular Specificities and Role of Cyclic GMP", *Biochimica et Biophysica Acta* 1980, 632, 35–46.

Richardson et al., "Astatine ($^{211}$At) as a Therapeutic Radionuclide. The Plasma: Blood Cell distribution in Vitro", *Nucl. Med. Biol. 13:* 583–584 (1986).

Sack, "Human Diarrheal Disease Caused by Enteroxigenic *Escherichia Coli*"*Ann Rev. Microbiol. 29:* 333–353 (1975).

Schulz, S. et al., "Cloning and Expression of Guanylin", *the J. Of Biol. Chem.* 1992, 267(23), 16019–16021.

Shimonishi et al., "Mode of Disulfide Bond Formation of a Heat–Stable Enterotoxin ($ST_h$) Produced by a Human Strain of Enterotoxigenic *Escherichia Coli*", *FEBS Letters 215:* 165–170 (1987).

So and McCarthy, "Nucleotide Sequence of the Bacterial Transposon Tn1681 Encoding a Heat–Stable (ST) Toxin and Its Identification in Enterotoxigenic *Escherichia Coli* Strains", *Proc. Natl. Acad. Sci. USA 77:* 4011–4015 (1980).

Spitler et al., "Therapy of Patients with Malignant Melanoma Using a Monoclonal Antimelanoma Antibody–Ricin A Chain Immunotoxin", *Cancer Research 47:* 1717–1723 (1987).

Steinsträβer et al., "Selection of Nuclides for Immunoscintigraphy/Immunotherapy", *J. Nucl. Med. 5:* 875 (1988).

Thompson et al, "Biological and Immunological Characteristics of $^{125}$I–4Tyr and –18Tyr *Escherichia coli* Heat–Stable Enterotoxin Species Purified by High–Performance Liquid Chromatography", *Analytical Biochemistry 148:* 26–36 (1985).

Thompson, M.R., "*Escherichia coli* Heat–Stable Enterotoxins and Their Receptors", *Pathol. Immunopathol.* 1987, 6, 103–116.

Thorpe et al., "New Coupling Agents for the Synthesis of Immunotoxins Containing a Hindered Disulfide Bond with Improved Stability In Vivo", *Cancer Research 47:* 5924–5931 (1987).

Vaandrager, A. et al., "Atriopeptins and *Escherichia coli* Enterotoxin ST Have Different Sites of Action in Mammalian Intestine", *Gastroenterology* 1992, 102(4), 1161–1169.

Waldman and O'Hanley, "Influence of a Glycine or Proline Substitution on the Functional Properties of a 14–Amino–Acid Analog of *Escherichia Coli* Heat–Stable Enterotoxin", *Infection and Immunity 57:* 2420–2424 (1989).

Wessels and Rogus, "Radionuclide Selection and Model Absorbed Dose Calculations for Radiolabeled Tumor Associated Antibodies", *Med. Phys. 11:* 638–645 (1984).

White, A. et al., "Opossum Kidney Contains a Functional Receptor for the *Escherichia coli* Heat–Stable Enterotoxin", *Biochemical and Biophysical Res. Comm.,* 1989, 159(1), 363–367.

Worrell et al., "Effect of Linkage Variation on Pharmacokinetics of Ricin A Chain–Antibody Conjugates in Normal Rats", *Anti–Cancer Drug Design 1:* 179–188 (1986).

Yoshimura et al, "Essential Structure for Full Enterotoxigenic Activity of Heat–Stable Enterotoxin Produced by Enterotoxigenic *Escherichia Coli*", *FEBS 2232 vol. 181:* 138–142 (1985).

Franz et al., "The Production of $^{99m}$Tc–Labeled Conjugated Antibodies Using A Cyclam–Based Bifunctional Chelating Agent", *J. Nucl. Med. Biol. 14:* 569–572 (1987).

Bailey's Textbook of Histology, 16th edition, Coperhaven et al., Williams and Wilkens, Baltimore, MD p. 404 (1975).

Wide, "Solid Phase Antigen–Antibody Systems", Radioimmunoassay Methods, Kirkham, Ed., E & S pp. 405–412 Livingstone, Edinburgh, (1971).

PCT International Search Report dated Aug. 7, 1997, 1 page.

SEQUENCE LISTING

```
(1) GENERAL INFORMATION:

(iii) NUMBER OF SEQUENCES: 54

(2) INFORMATION FOR SEQ ID NO:1:

(i) SEQUENCE CHARACTERISTICS:
          (A) LENGTH: 57 base pairs
          (B) TYPE: nucleic acid
          (C) STRANDEDNESS: double
          (D) TOPOLOGY: both (ii) MOLECULE TYPE: cDNA (ix) FEATURE:
          (A) NAME/KEY: CDS
          (B) LOCATION: 1..57

(xi) SEQUENCE DESCRIPTION: SEQ ID NO:1:
```

```
AAC AAC ACA TTT TAC TGC TGT GAA CTT TGT TGT AAT CCT GCC TGT GCT         48
Asn Asn Thr Phe Tyr Cys Cys Glu Leu Cys Cys Asn Pro Ala Cys Ala
  1               5                  10                  15

GGA TGT TAT                                                             57
Gly Cys Tyr
```

(2) INFORMATION FOR SEQ ID NO:2:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:2:

```
Asn Asn Thr Phe Tyr Cys Cys Glu Leu Cys Cys Asn Pro Ala Cys Ala
  1               5                  10                  15

Gly Cys Tyr
```

(2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:3:

```
Asn Thr Phe Tyr Cys Cys Glu Leu Cys Cys Tyr Pro Ala Cys Ala Gly
  1               5                  10                  15

Cys Asn
```

(2) INFORMATION FOR SEQ ID NO:4:

(i) SEQUENCE CHARACTERISTICS:
        (A) LENGTH: 57 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 1..57

(xi) SEQUENCE DESCRIPTION: SEQ ID NO:4:

```
AAT AGT AGC AAT TAC TGC TGT GAA TTG TGT TGT AAT CCT GCT TGT AAC         48
Asn Ser Ser Asn Tyr Cys Cys Glu Leu Cys Cys Asn Pro Ala Cys Asn
  1               5                  10                  15

GGG TGC TAT                                                             57
Gly Cys Tyr
```

(2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:5:

```
Asn Ser Ser Asn Tyr Cys Cys Glu Leu Cys Cys Asn Pro Ala Cys Asn
  1               5                  10                  15
```

Gly Cys Tyr (2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

Pro Asn Thr Cys Glu Ile Cys Ala Tyr Ala Ala Cys Thr Gly Cys
1             5                10             15

(2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:7:

Asn Asn Thr Phe Tyr Cys Cys Glu Leu Cys Cys Asn Pro Ala Cys Ala
1             5                10             15

Gly Cys (2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:8:

Asn Thr Phe Tyr Cys Cys Glu Leu Cys Cys Asn Pro Ala Cys Ala Gly
1             5                10             15

Cys (2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:9:

Thr Phe Tyr Cys Cys Glu Leu Cys Cys Asn Pro Ala Cys Ala Gly Cys
1             5                10             15

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:10:

-continued

```
Phe Tyr Cys Cys Glu Leu Cys Cys Asn Pro Ala Cys Ala Gly Cys
 1               5                  10                  15
```

(2) INFORMATION FOR SEQ ID NO:11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:11:

```
Tyr Cys Cys Glu Leu Cys Cys Asn Pro Ala Cys Ala Gly Cys
 1               5                  10
```

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:12:

```
Cys Cys Glu Leu Cys Cys Asn Pro Ala Cys Ala Gly Cys
 1               5                  10
```

(2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:13:

```
Asn Thr Phe Tyr Cys Cys Glu Leu Cys Cys Asn Pro Ala Cys Ala Gly
 1               5                  10                  15
Cys Tyr
```

(2) INFORMATION FOR SEQ ID NO:14:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:14:

```
Thr Phe Tyr Cys Cys Glu Leu Cys Cys Asn Pro Ala Cys Ala Gly Cys
 1               5                  10                  15
Tyr
```

(2) INFORMATION FOR SEQ ID NO:15:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:15:

```
Phe Tyr Cys Cys Glu Leu Cys Cys Asn Pro Ala Cys Ala Gly Cys Tyr
 1               5                  10                  15
```

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:16:

```
Tyr Cys Cys Glu Leu Cys Cys Asn Pro Ala Cys Ala Gly Cys Tyr
 1               5                  10                  15
```

(2) INFORMATION FOR SEQ ID NO:17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:17:

```
Cys Cys Glu Leu Cys Cys Asn Pro Ala Cys Ala Gly Cys Tyr
 1               5                  10
```

(2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:18:

```
Asn Thr Phe Tyr Cys Cys Glu Leu Cys Cys Tyr Pro Ala Cys Ala Gly
 1               5                  10                  15
Cys
```

(2) INFORMATION FOR SEQ ID NO:19:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:19:

```
Thr Phe Tyr Cys Cys Glu Leu Cys Cys Tyr Pro Ala Cys Ala Gly Cys
 1               5                  10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:20:

```
Phe Tyr Cys Cys Glu Leu Cys Cys Tyr Pro Ala Cys Ala Gly Cys
 1               5                  10                  15
```

(2) INFORMATION FOR SEQ ID NO:21:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:21:

```
Tyr Cys Cys Glu Leu Cys Cys Tyr Pro Ala Cys Ala Gly Cys
 1               5                  10
```

(2) INFORMATION FOR SEQ ID NO:22:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:22:

```
Cys Cys Glu Leu Cys Cys Tyr Pro Ala Cys Ala Gly Cys
 1               5                  10
```

(2) INFORMATION FOR SEQ ID NO:23:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:23:

```
Thr Phe Tyr Cys Cys Glu Leu Cys Cys Tyr Pro Ala Cys Ala Gly Cys
 1               5                  10                  15
Asn
```

(2) INFORMATION FOR SEQ ID NO:24:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:24:

```
Phe Tyr Cys Cys Glu Leu Cys Cys Tyr Pro Ala Cys Ala Gly Cys Asn
 1               5                  10                  15
```

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:25:

```
Tyr Cys Cys Glu Leu Cys Cys Tyr Pro Ala Cys Ala Gly Cys Asn
 1               5                  10                  15
```

```
(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:26:

Cys Cys Glu Leu Cys Cys Tyr Pro Ala Cys Ala Gly Cys Asn
  1               5                  10

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:27:

Asn Ser Ser Asn Tyr Cys Cys Glu Leu Cys Cys Asn Pro Ala Cys Thr
  1               5                  10                  15

Gly Cys (2) INFORMATION FOR SEQ ID NO:28:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:28:

Ser Ser Asn Tyr Cys Cys Glu Leu Cys Cys Asn Pro Ala Cys Thr Gly
  1               5                  10                  15

Cys (2) INFORMATION FOR SEQ ID NO:29:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:29:

Ser Asn Tyr Cys Cys Glu Leu Cys Cys Asn Pro Ala Cys Thr Gly Cys
  1               5                  10                  15

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:30:

Asn Tyr Cys Cys Glu Leu Cys Cys Asn Pro Ala Cys Thr Gly Cys
  1               5                  10                  15
```

(2) INFORMATION FOR SEQ ID NO:31:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:31:

Tyr Cys Cys Glu Leu Cys Cys Asn Pro Ala Cys Thr Gly Cys
 1               5                  10

(2) INFORMATION FOR SEQ ID NO:32:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:32:

Cys Cys Glu Leu Cys Cys Asn Pro Ala Cys Thr Gly Cys
 1               5                  10

(2) INFORMATION FOR SEQ ID NO:33:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:33:

Ser Ser Asn Tyr Cys Cys Glu Leu Cys Cys Asn Pro Ala Cys Thr Gly
 1               5                  10                  15

Cys Tyr (2) INFORMATION FOR SEQ ID NO:34:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:34:

Ser Asn Tyr Cys Cys Glu Leu Cys Cys Asn Pro Ala Cys Thr Gly Cys
 1               5                  10                  15

Tyr (2) INFORMATION FOR SEQ ID NO:35:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:35:

Asn Tyr Cys Cys Glu Leu Cys Cys Asn Pro Ala Cys Thr Gly Cys Tyr
 1               5                  10                  15

-continued

```
(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:36:

Tyr Cys Cys Glu Leu Cys Cys Asn Pro Ala Cys Thr Gly Cys Tyr
 1               5                  10                  15

(2) INFORMATION FOR SEQ ID NO:37:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:37:

Cys Cys Glu Leu Cys Cys Asn Pro Ala Cys Thr Gly Cys Tyr
 1               5                  10

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:38:

Asn Thr Phe Tyr Cys Cys Glu Leu Cys Cys Asn Pro Ala Cys Ala Gly
 1               5                  10                  15

Cys Tyr (2) INFORMATION FOR SEQ ID NO:39:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:39:

Asn Thr Phe Tyr Cys Cys Glu Leu Cys Cys Ala Pro Ala Cys Ala Gly
 1               5                  10                  15

Cys Tyr (2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:40:

Asn Thr Phe Tyr Cys Cys Glu Leu Cys Cys Asn Ala Ala Cys Ala Gly
 1               5                  10                  15

Cys Tyr
```

(2) INFORMATION FOR SEQ ID NO:41:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:41:

```
Asn Thr Phe Tyr Cys Cys Glu Leu Cys Cys Asn Pro Ala Cys Ala Gly
  1               5                  10                  15
Cys
```

(2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:42:

```
Tyr Cys Cys Glu Leu Cys Cys Asn Pro Ala Cys Ala Gly Cys Tyr
  1               5                  10                  15
```

(2) INFORMATION FOR SEQ ID NO:43:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:43:

```
Tyr Cys Cys Glu Leu Cys Cys Asn Pro Ala Cys Ala Gly Cys
  1               5                  10
```

(2) INFORMATION FOR SEQ ID NO:44:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:44:

```
Cys Cys Glu Leu Cys Cys Asn Pro Ala Cys Ala Gly Cys Tyr
  1               5                  10
```

(2) INFORMATION FOR SEQ ID NO:45:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:45:

```
Cys Cys Glu Leu Cys Cys Asn Pro Ala Cys Ala Gly Cys
  1               5                  10
```

(2) INFORMATION FOR SEQ ID NO:46:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:46:

```
Gln Ala Cys Asp Pro Pro Ser Pro Pro Ala Glu Val Cys Cys Asp Val
  1               5                  10                  15
Cys Cys Asn Pro Ala Cys Ala Gly Cys
               20                  25
```

(2) INFORMATION FOR SEQ ID NO:47:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:47:

```
Ile Asp Cys Cys Ile Cys Cys Asn Pro Ala Cys Phe Gly Cys Leu Asn
  1               5                  10                  15
```

(2) INFORMATION FOR SEQ ID NO:48:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:48:

```
Ser Ser Asp Trp Asp Cys Cys Asp Val Cys Cys Asn Pro Ala Cys Ala
  1               5                  10                  15
Gly Cys
```

(2) INFORMATION FOR SEQ ID NO:49:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:49:

```
Asn Ser Ser Asn Tyr Cys Cys Glu Leu Cys Cys Tyr Pro Ala Cys Thr
  1               5                  10                  15
Gly Cys Tyr
```

(2) INFORMATION FOR SEQ ID NO:50:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:50:

```
Cys Cys Asp Val Cys Cys Asn Pro Ala Cys Thr Gly Cys
```

-continued

```
                1               5                      10
```

(2) INFORMATION FOR SEQ ID NO:51:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:51:

```
Cys Cys Asp Val Cys Cys Tyr Pro Ala Cys Thr Gly Cys Tyr
  1               5                      10
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:52:

```
Cys Cys Asp Leu Cys Cys Asn Pro Ala Cys Ala Gly Cys Tyr
  1               5                      10
```

(2) INFORMATION FOR SEQ ID NO:53:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:53:

```
Cys Cys Gln Leu Cys Cys Asn Pro Ala Cys Thr Gly Cys Tyr
  1               5                      10
```

(2) INFORMATION FOR SEQ ID NO:54:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:54:

```
Pro Gly Thr Cys Glu Ile Cys Ala Tyr Ala Ala Cys Thr Gly Cys
  1               5                      10                  15
```

COMPOSITIONS THAT SPECIFICALLY BIND TO COLORECTAL CANCER CELLS AND METHODS OF USING THE SAME

CROSS REFERENCE TO RELATED APPLICATIONS

This application is the U.S. National Phase filing PCT Application PCT/US94/12232, filed Oct. 26, 1994, which claims priority as a continuation-in-part application to U.S. Ser. No. 08/141,892 filed Oct. 26, 1993, issued as U.S. Pat. No. 5,518,888, and as a continuation-in-part application of U.S. Ser. No. 08/305,056 filed Sep. 13, 1994, issued as U.S. Pat. No. 5,601,990.

ACKNOWLEDGMENT OF GOVERNMENT RIGHTS

This invention was made with Government support under grant number DK43805-01A2 awarded by the National Institutes of Health. The Government has certain rights in this invention.

FIELD OF THE INVENTION

The present invention relates to compounds which comprise a receptor ligand moiety that binds to the ST receptor conjugated to a therapeutic or imaging moiety and to uses in the detection and treatment of colorectal tumors, particularly metastasized tumors. The present invention relates to compositions and kits for and methods of detecting metastasized colorectal tumor cells in samples, for determining whether or not a tumor is colorectal in origin, and for evaluating the extent of invasive activity of colorectal tumor cells in samples from the colon. This application is related to U.S. Ser. No. 08/141,892 filed Oct. 26, 1993 and U.S. Ser. No. 08/305,056 filed Sep. 13, 1994, the disclosures of both of which are incorporated herein by reference.

BACKGROUND OF THE INVENTION

Colorectal cancer is the third most common neoplasm worldwide. The mortality rate of newly diagnosed large bowel cancer approaches 50% and there has been little improvement over the past 40 years. Most of this mortality reflects local, regional and distant metastases.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. Similarly, diagnosis of metastatic or recurrent disease earlier potentially carries with it a better prognosis.

Although current radiotherapeutic agents, chemotherapeutic agents and biological toxins are potent cytotoxins, they do not discriminate between normal and malignant cells, producing adverse effects and dose-limiting toxicities. Over the past decade, a novel approach has been employed to more specifically target agents to tumor cells, involving the conjugation of an active agent to molecules which binds preferentially to antigens that exist predominantly on tumor cells. These conjugates can be administered systemically and specifically bind to the targeted tumor cells. Theoretically, targeting permits uptake by cells of cytotoxic agents at concentrations which do not produce serious toxicities in normal tissues. Also, selective binding to targeted tumor cells facilitates detection of occult tumor and is therefore useful in designing imaging agents. Molecular targeting predominantly has employed monoclonal antibodies generated to antigens selectively expressed on tumor cells.

Immunoscintigraphy using monoclonal antibodies directed at tumor-specific markers has been employed to diagnose colorectal cancer. Monoclonal antibodies against carcinoembryonic antigen (CEA) labelled with $^{99}$Technetium identified 94% of patients with recurrent tumors. Similarly, $^{111}$Indium-labelled anti-CEA monoclonal antibodies successfully diagnosed 85% of patients with recurrent colorectal carcinoma who were not diagnosed by conventional techniques. $^{125}$Iodine-labelled antibodies have been effective in localizing more than 80% of the pathologically-confirmed recurrences by intraoperative gamma probe scanning.

Monoclonal antibodies have also been employed to target specific therapeutic agents in colorectal cancer. Preclinical studies demonstrated that anti-CEA antibodies labelled with $^{90}$Yttrium inhibited human colon carcinoma xenografts in nude mice. Antibodies generated to colorectal cancer cells and coupled to mitomycin C or neocarzinostatin demonstrated an anti-tumor effect on human colon cancer xenografts in nude mice and 3 patients with colon cancer.

Similar results in animals were obtained with monoclonal antibodies conjugated to ricin toxin A chain.

Due to the sensitivity, specificity, and adverse-effect profile of monoclonal antibodies, the results obtained using monoclonal antibody-based therapeutics have shown them to be less than ideal targeting tools. Although monoclonal antibodies have been generated to antigens selectively expressed on tumors, no truly cancer-specific antibody has been identified. Most antigens expressed on neoplastic cells appear to be quantitatively increased in these compared to normal cells but the antigens are nonetheless often present in normal cells. Thus, antibodies to such determinants can react with non-neoplastic tissues, resulting in significant toxicities. Also, antibodies are relatively large molecules and consequently, often evoke an immune response in patients. These immune responses can result in significant toxicities in patients upon re-exposure to the targeting agents and can prevent targeting by the monoclonal due to immune complex formation with degradation and excretion. Finally, binding of antibodies to tumor cells may be low and targeted agents may be delivered to cells in quantities insufficient to achieve detection or cytotoxicity.

There remains a need for compositions which can specifically target metastasized colorectal cancer cells. There is a need for imaging agents which can specifically bind to metastasized colorectal cancer cells. There is a need for improved methods of imaging metastasized colorectal cancer cells. There is a need for therapeutic agents which can specifically bind to metastasized colorectal cancer cells. There is a need for improved methods of treating individuals who are suspected of suffering from colorectal cancer cells, especially individuals who are suspected of suffering from metastasis of colorectal cancer cells.

SUMMARY OF THE INVENTION

The present invention relates to conjugated compounds which comprises an ST receptor binding moiety and a radiostable active moiety.

The present invention relates to a pharmaceutical composition comprising a pharmaceutically acceptable carrier or diluent, and a conjugated compound which comprises an ST receptor binding moiety and a radiostable active moiety. The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises an ST receptor binding moiety and a radiostable active moiety.

The present invention relates to a pharmaceutical composition comprising a pharmaceutically acceptable carrier or diluent, and conjugated compound that comprises an ST receptor binding moiety and a radioactive active moiety wherein the conjugated compound is present in an amount effective for therapeutic or diagnostic use in humans suffering from colorectal cancer.

The present invention relates to a method of radioimaging metastasized colorectal cancer cells comprising the steps of first administering to an individual suspected of having metastasized colorectal cancer cells, a pharmaceutical composition that comprises a pharmaceutically acceptable carrier or diluent, and conjugated compound that comprises an ST receptor binding moiety and a radioactive active moiety wherein the conjugated compound is present in an amount effective for diagnostic use in humans suffering from colorectal cancer and then detecting the localization and accumulation of radioactivity in the individual's body.

The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises an ST receptor binding moiety and a radioactive active moiety.

The present invention relates to in vitro methods of determining whether or not an individual has metastasized colorectal cancer cells. The present invention relates to in vitro methods of examining samples of non-colorectal tissue and body fluids from an individual to determine whether or not ST receptor protein, which is a protein that is specific to colorectal cells including colorectal tumor cells, is being expressed by cells outside of the colorectal tract. The presence of the ST receptor protein or of nucleic acid molecules that are indicative of expression of the ST receptor protein is evidence that the individual is suffering from metastasized colorectal cancer.

The present invention relates to in vitro methods of determining whether or not tumor cells are colorectal in origin. The present invention relates to in vitro methods of diagnosing whether or not an individual suffering from cancer is suffering from colorectal cancer. The present invention relates to in vitro methods of examining samples of tumors from an individual to determine whether or not ST receptor protein, which is a protein that is specific to colorectal cells including colorectal tumor cells, is being expressed by the tumor cells. The presence of the ST receptor protein or of nucleic acid molecules that are indicative of expression of the ST receptor protein is evidence that the individual is suffering from colorectal cancer.

The present invention relates to in vitro kits for practicing the methods of the invention and to reagents and compositions useful as components in such in vitro kits of the invention.

DESCRIPTION OF PREFERRED EMBODIMENTS OF THE INVENTION

The invention is related to U.S. Ser. No. 08/141,892 filed Oct. 26, 1993 and U.S. Ser. No. 08/305,056 filed Sep. 13, 1994, the disclosures of both of which are incorporated herein by reference.

As used herein, the terms "ST" and "native ST" are used interchangeably and are meant to refer to heat-stable toxin (ST) which is a peptide produced by *E. coli*, as well as other organisms. STs are naturally occurring peptides which 1) are naturally produced by organisms, 2) bind to the ST receptor and 3) activate the signal cascade that mediates ST-induced diarrhea.

As used herein, the term "ST receptor" is meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "ST receptor ligand" is meant to refer to compounds which specifically bind to the ST receptor. ST is an ST receptor ligand. An ST receptor ligand may be a peptide or a non-peptide.

As used herein, the term "ST receptor binding peptide" is meant to refer to ST receptor ligands that are peptides.

As used herein, the term "ST peptides" is meant to refer to ST receptor binding peptides selected from the group consisting of SEQ ID NO:2, SEQ ID NO:3, SEQ ID NOS:5–54 and fragments and derivatives thereof.

As used herein, the term "fragment" is meant to refer to peptide a) which has an amino acid sequence identical to a portion of an ST receptor binding peptide and b) which is capable of binding to the ST receptor.

As used herein, the term "derivative" is meant to refer to a peptide a) which has an amino acid sequence substantially identical to at least a portion of an ST receptor binding peptide and b) which is capable of binding to the ST receptor.

As used herein, the term "substantially identical" is meant to refer to an amino acid sequence that is the same as the amino acid sequence of an ST peptide except some of the residues are deleted or substituted with conservative amino acids or additional amino acids are inserted.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the metastasized cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "ST receptor binding moiety" is meant to refer to the portion of a conjugated compound that constitutes an ST receptor ligand.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises an ST receptor binding moiety and an active moiety and which is capable of binding to the ST receptor. Conjugated compounds according to the present invention comprise a portion which constitutes an ST receptor ligand and a portion which constitutes an active agent. Thus, conjugated compounds according to the present invention are capable of specifically binding to the ST receptor and include a portion which is a therapeutic agent or imaging agent. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the ST receptor ligand and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to metastasized colorectal cancer" is meant to refer to an individual who is at a particular risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence.

ST, which is produced by *E. coli*, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is noncovalent and occurs in a concentration-dependent and saturable fashion. Once bound, ST-ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen. Therefore, the apical location of ST receptors isolates these receptors from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express ST receptors. Conversely, tissue samples taken from tissue outside of the intestinal tract do not normally contain cells which express ST receptors.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors.

An effort was undertaken to determine the proportion of colorectal tumors which have the ST receptor. Each of the tumors tested were independently confirmed to be colorectal cancer by standard techniques of surgical pathology. Every one of the colorectal cancer tumors tested, including local colorectal tumors and metastasized colorectal tumors (liver, lung, lymph node, peritoneum, ovary) possessed ST receptors. In each case, the affinity and density of receptors was amenable for targeting. Normal liver, lymphnode, peritoneum, gall bladder, ovary, stomach, kidney and lung cells were found not to possess ST receptors.

When such cancer cells metastasize, the metastasized cancer cells continue to produce and display the ST receptor. The expression of ST receptors on the surfaces of metastatic tumors provides a target for selective binding of conjugated compositions. ST receptors permit the absolutely specific targeting of therapeutic and diagnostic agents that are conjugated to ST receptor ligands to metastatic colorectal cancer cells.

According to some embodiments of the invention, compositions and methods are provided for detecting, imaging, or treating colorectal tumors in an individual.

The conjugated compositions of the present invention are useful for targeting cells that line the inner intestine wall including those cancer cells derived from such cells, particularly metastasized cancer cells derived from such cells. The conjugated compositions of the present invention which are administered outside the intestinal tract such as those administered in the circulatory system will remain segregated from the cells that line the intestinal tract and will bind only to cells outside the intestinal tract which are derived from the intestinal tract such as metastasized colorectal cells. The conjugated compositions will not bind to non-colorectal derived cells. Thus, the active moieties of conjugated compositions administered outside the intestinal tract are delivered to cells which are derived from the intestinal tract such as metastasized colorectal cells but will not be delivered to any other cells.

Therapeutic and diagnostic pharmaceutical compositions of the present invention include conjugated compounds specifically targeted to metastatic disease. These conjugated compounds include ST receptor binding moieties which do not bind to cells of normal tissue in the body except cells of the intestinal tract since the cells of other tissues do not possess ST receptors. Unlike normal colorectal cells and localized colorectal cancer cells, metastasized colorectal cancer cells are accessible to substances administered outside the intestinal tract, for example administered in the circulatory system. The only ST receptors in normal tissue exist in the apical membranes of intestinal mucosa cells and these receptors are effectively isolated from the targeted cancer chemotherapeutics and imaging agents administered outside the intestinal tract by the intestinal mucosa barrier. Thus, metastasized colorectal cells may be targeted by conjugated compounds of the present invention by introducing such compounds outside the intestinal tract such as for example by administering pharmaceutical compositions that comprise conjugated compounds into the circulatory system.

One having ordinary skill in the art can readily identify individuals suspected of suffering from colorectal cancer and metastasized colorectal cells. In those individuals diagnosed with colorectal cancer, it is standard therapy to suspect metastasis and aggressively attempt to eradicate metastasized cells. The present invention provides pharmaceutical compositions and methods for imaging and thereby will more definitively diagnose metastasis. Further, the present invention provides pharmaceutical compositions comprising therapeutic agents and methods for specifically targeting and eliminating metastasized colorectal cancer cells. Further, the present invention provides pharmaceutical compositions that comprise therapeutics and methods for specifically eliminating colorectal cancer cells.

The pharmaceutical compositions which comprise conjugated compositions of the present invention may be used to diagnose or treat individuals suffering from localized colorectal tumors, that is primary or non-metastatic colorectal tumors if these have penetrated the basement membrane underlying the mucosa into the submucosa where there is abundant blood supply to which they have access. Penetration into the submucosa circumvents the mucosal barrier resulting in the ability of conjugated compositions introduced into the circulatory system to interact with these tumors.

The present invention relies upon the use of an ST receptor binding moiety in a conjugated composition. The ST receptor binding moiety is essentially a portion of the conjugated composition which acts as a ligand to the ST receptor and thus specifically binds to these receptors. The conjugated composition also includes an active moiety which is associated with the ST receptor binding moiety; the active moiety being an active agent which is either useful to image, target, neutralize or kill the cell.

According to the present invention, the ST receptor binding moiety is the ST receptor ligand portion of a conjugated composition. In some embodiments, the ST receptor ligand may be native ST.

Native ST has been isolated from a variety of organisms including *E. coli*, Yersinia, Enterobacter, and others. In nature, the toxins are generally encoded on a plasmid which can "jump" between different species. Several different toxins have been reported to occur in different species. These toxins all possess significant sequence homology, they all bind to ST receptors and they all activate guanylate cyclase, producing diarrhea.

ST has been both cloned and synthesized by chemical techniques. The cloned or synthetic molecules exhibit binding characteristics which are similar to native ST. Native ST isolated from *E. coli* is 18 or 19 amino acids in length. The smallest "fragment" of ST which retains activity is the 13 amino acid core peptide extending toward the carboxy terminal from cysteine 6 to cysteine 18 (of the 19 amino acid form). Analogues of ST have been generated by cloning and by chemical techniques. Small peptide fragments of the native ST structure which include the structural determinant that confers binding activity may be constructed. Once a structure is identified which binds to ST receptors, non-peptide analogues mimicking that structure in space are designed.

SEQ ID NO:1 discloses a nucleotide sequence which encodes 19 amino acid ST, designated ST Ia, reported by So and McCarthy (1980) *Proc. Natl. Acad. Sci. USA* 77:4011, which is incorporated herein by reference.

The amino acid sequence of ST Ia is disclosed in SEQ ID NO:2.

SEQ ID NO:3 discloses the amino acid sequence of an 18 amino acid peptide which exhibits ST activity, designated ST I*, reported by Chan and Giannella (1981) *J. Biol. Chem.* 256:7744, which is incorporated herein by reference.

SEQ ID NO:4 discloses a nucleotide sequence which encodes 19 amino acid ST, designated ST Ib, reported by Mosely et al. (1983) *Infect. Immun.* 39:1167, which is incorporated herein by reference.

The amino acid sequence of ST Ib is disclosed in SEQ ID NO:5.

A 15 amino acid peptide called guanylin which has about 50% sequence homology to ST has been identified in mammalian intestine (Currie, M. G. et al. (1992) *Proc. Natl. Acad Sci. USA* 89:947–951, which is incorporated herein by reference). Guanylin binds to ST receptors and activates guanylate cyclase at a level of about 10- to 100-fold less than native ST. Guanylin may not exist as a 15 amino acid peptide in the intestine but rather as part of a larger protein in that organ. The amino acid sequence of guanylin from rodent is disclosed as SEQ ID NO:6.

SEQ ID NO:7 is an 18 amino acid fragment of SEQ ID NO:2. SEQ ID NO:8 is a 17 amino acid fragment of SEQ ID NO:2. SEQ ID NO:9 is a 16 amino acid fragment of SEQ ID NO:2. SEQ ID NO:10 is a 15 amino acid fragment of SEQ ID NO:2. SEQ ID NO:11 is a 14 amino acid fragment of SEQ ID NO:2. SEQ ID NO:12 is a 13 amino acid fragment of SEQ ID NO:2. SEQ ID NO:13 is an 18 amino acid fragment of SEQ ID NO:2. SEQ ID NO:14 is a 17 amino acid fragment of SEQ ID NO:2. SEQ ID NO:15 is a 16 amino acid fragment of SEQ ID NO:2. SEQ ID NO:16 is a 15 amino acid fragment of SEQ ID NO:2. SEQ ID NO:17 is a 14 amino acid fragment of SEQ ID NO:2.

SEQ ID NO:18 is a 17 amino acid fragment of SEQ ID NO:3. SEQ ID NO:19 is a 16 amino acid fragment of SEQ ID NO:3. SEQ ID NO:20 is a 15 amino acid fragment of SEQ ID NO:3. SEQ ID NO:21 is a 14 amino acid fragment of SEQ ID NO:3. SEQ ID NO:22 is a 13 amino acid fragment of SEQ ID NO:3. SEQ ID NO:23 is a 17 amino acid fragment of SEQ ID NO:3. SEQ ID NO:24 is a 16 amino acid fragment of SEQ ID NO:3. SEQ ID NO:25 is a 15 amino acid fragment of SEQ ID NO:3. SEQ ID NO:26 is a 14 amino acid fragment of SEQ ID NO:3.

SEQ ID NO:27 is an 18 amino acid fragment of SEQ ID NO:5. SEQ ID NO:28 is a 17 amino acid fragment of SEQ ID NO:5. SEQ ID NO:29 is a 16 amino acid fragment of SEQ ID NO:5. SEQ ID NO:30 is a 15 amino acid fragment of SEQ ID NO:5. SEQ ID NO:31 is a 14 amino acid fragment of SEQ ID NO:5. SEQ ID NO:32 is a 13 amino acid fragment of SEQ ID NO:5. SEQ ID NO:33 is an 18 amino acid fragment of SEQ ID NO:5. SEQ ID NO:34 is a 17 amino acid fragment of SEQ ID NO:5. SEQ ID NO:35 is a 16 amino acid fragment of SEQ ID NO:5. SEQ ID NO:36 is a 15 amino acid fragment of SEQ ID NO:5. SEQ ID NO:37 is a 14 amino acid fragment of SEQ ID NO:5.

SEQ ID NO:27, SEQ ID NO:31, SEQ ID NO:36 AND SEQ ID NO:37 are disclosed in Yoshimura, S., et al. (1985) *FEBS Lett.* 181:138, which is incorporated herein by reference.

SEQ ID NO:38, SEQ ID NO:39 and SEQ ID NO:40, which are derivatives of SEQ ID NO:3, are disclosed in Waldman, S. A. and O'Hanley, P. (1989) *Infect. Immun.* 57:2420, which is incorporated herein by reference.

SEQ ID NO:41, SEQ ID NO:42, SEQ ID NO:43, SEQ ID NO:44 and SEQ ID NO:45, which are a derivatives of SEQ ID NO:3, are disclosed in Yoshimura, S., et al. (1985) *FEBS Lett.* 181:138, which is incorporated herein by reference.

SEQ ID NO:46 is a 25 amino acid peptide derived from *Y. enterocolitica* which binds to the ST receptor.

SEQ ID NO:47 is a 16 amino acid peptide derived from *V. cholerae* which binds to the ST receptor. SEQ ID NO:47 is reported in Shimonishi, Y., et al. *FEBS Lett.* 215:165, which is incorporated herein by reference.

SEQ ID NO:48 is an 18 amino acid peptide derived from *Y. enterocolitica* which binds to the ST receptor. SEQ ID NO:48 is reported in Okamoto, K., et al. *Infec. Immun.* 55:2121, which is incorporated herein by reference.

SEQ ID NO:49, is a derivative of SEQ ID NO:5.

SEQ ID NO:50, SEQ ID NO:51, SEQ ID NO:52 and SEQ ID NO:53 are derivatives.

SEQ ID NO:54 is the amino acid sequence of guanylin from human.

In some preferred embodiments, conjugated compounds comprise ST receptor binding moieties that comprise amino acid sequences selected from the group consisting of SEQ ID NO:2, SEQ ID NO:3, SEQ ID NOS:5–54 and fragments and derivatives thereof.

Those having ordinary skill in the art can readily design and produce derivatives having substantially identical amino acid sequences of ST peptides with deletions and/or insertions and/or conservative substitutions of amino acids. For example, following what are referred to as Dayhof's rules for amino acid substitution (Dayhof, M. D. (1978) *Nat. Biomed. Res. Found.*, Washington, D.C. Vol. 5, supp. 3), amino acid residues in a peptide sequence may be substituted with comparable amino acid residues. Such substitutions are well-known and are based the upon charge and structural characteristics of each amino acid. Derivatives include fragments of ST receptor binding peptides with deletions and/or insertions and/or conservative substitutions.

In some embodiments, ST receptor binding peptides comprise D amino acids. As used herein, the term "D amino acid peptides" is meant to refer to ST receptor binding peptides, fragments or derivatives which comprise at least one and preferably a plurality of D amino acids which are capable of binding to the ST receptor. The use of D amino acid peptides is desirable as they are less vulnerable to degradation and therefore have a longer half-life. D amino acid peptides comprising mostly all or consisting of D amino acids may comprise amino acid sequences in the reverse order of ST receptor binding peptides which are made up of L amino acids.

In some embodiments, ST receptor binding peptides, including D amino acid peptides, are conformationally restricted to present and maintain the proper structural conformation for binding to the ST receptor. The compositions may comprise additional amino acid residues required to achieve proper three dimensional conformation including residues which facilitate circularization or desired folding.

It is preferred that the ST receptor ligand used as the ST receptor binding moiety be as small as possible. Thus it is preferred that the ST receptor ligand be a non-peptide small molecule or small peptide, preferably less than 25 amino acids, more preferably less than 20 amino acids. In some embodiments, the ST receptor ligand which constitute the ST receptor binding moiety of a conjugated composition is less than 15 amino acids. ST receptor binding peptide comprising less than 10 amino acids and ST receptor binding peptide less than 5 amino acids may be used as ST binding moieties according to the present invention. It is within the scope of the present invention to include larger molecules which serve as ST receptor binding moieties including, but not limited to molecules such as antibodies, FAbs and F(Ab)2s which specifically bind to ST receptor.

An assay may be used to test both peptide and nonpeptide compositions to determine whether or not they are ST receptor ligands or, to test conjugated compositions to determine if they possess ST receptor binding activity. Such compositions that specifically bind to ST receptors can be identified by a competitive binding assay. The competitive binding assay is a standard technique in pharmacology which can be readily performed by those having ordinary skill in the art using readily available starting materials. Competitive binding assays, ST receptor binding assays, have been shown to be effective for identifying compositions that specifically bind to ST receptors. Briefly, the assay consists of incubating a preparation of ST receptors (e.g. intestinal membranes from rat intestine, human intestine, T84 cells) with a constant concentration ($1 \times 10^{-10}$ M to $5 \times 10^{-10}$ M) of $^{125}$I-ST (any ST receptor ligand such as native STs SEQ ID NO:2, SEQ ID NO:3 or SEQ ID NO:5 may be used) and a known concentration of a test compound. As a control, a duplicate preparation of ST receptors are incubated with a duplicate concentration of 125I-ST in the absence of test compound. Assays are incubated to equilibrium (2 hours) and the amount of $^{125}$I-ST bound to receptors is quantified by standard techniques. The ability of the test compound to bind to receptors is measured as its ability to prevent (compete with) the $^{125}$I-ST from binding. Thus, in assays containing the test compound which bind to the receptor, there will be less radioactivity associated with the receptors. This assay, which is appropriate for determining the ability of any molecule to bind to ST receptors, is a standard competitive binding assay which can be readily employed by those having ordinary skill in the art using readily available starting materials.

ST may be isolated from natural sources using standard techniques. Additionally, ST receptor binding peptides and conjugated compositions or portions thereof which are peptides may be prepared routinely by any of the following known techniques.

ST receptor binding peptides and conjugated compositions or portions thereof which are peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

ST receptor binding peptides and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce an ST receptor binding peptide which occurs in nature, one having ordinary skill in the art can, using well-known techniques, obtain a DNA molecule encoding the ST receptor binding peptides from the genome of the organism that produces the ST receptor binding peptide and insert that DNA molecule into a commercially available expression vector for use in well-known expression systems.

Likewise, one having ordinary skill in the art can, using well known techniques, combine a DNA molecule that encodes an ST receptor binding peptide, such as SEQ ID NO:1 and SEQ ID NO:4, which can be obtained from the genome of the organism that produces the ST, with DNA that encodes a toxin, another active agent that is a peptide or additionally, any other amino acid sequences desired to be adjacent to the ST receptor binding peptide amino acid sequence in a single peptide and insert that DNA molecule into a commercially available expression vector for use in well-known expression systems.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art may use these or other commercially available expression vectors and systems or produce vectors using well-known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well-known techniques, isolate the protein that is produced.

According to the present invention, the active moiety may be a therapeutic agent or an imaging agent. One having ordinary skill in the art can readily recognize the advantages of being able to specifically target metastasized colorectal cells with an ST receptor ligand and conjugate such a ligand with many different active agents.

Chemotherapeutics useful as active moieties which when conjugated to an ST receptor binding moiety are specifically delivered to metastasized colorectal cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to an ST receptor binding moiety, the conjugated composition is specifically delivered to a metastasized colorectal cell by way of the ST receptor binding moiety and the toxin moiety kills the cell. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. As discussed above, when protein toxins are employed with ST receptor binding peptides, conjugated compositions may be produced using recombinant DNA techniques. Briefly, a recombinant DNA molecule can be constructed which encodes both the ST receptor ligand and the toxin on a chimeric gene. When the chimeric gene is expressed, a fusion protein is produced which includes an ST receptor binding moiety and an active moiety. Protein toxins are also useful to form conjugated compounds with ST receptor binding peptides through non-peptidyl bonds.

In addition, there are other approaches for utilizing active agents for the treatment of cancer. For example, conjugated compositions may be produced which include an ST binding moiety and an active moiety which is an active enzyme. The ST binding moiety specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/etoposidephosphate. In such a case, the alkaline phosphatase is conjugated to an ST receptor binding ligand. The conjugated compound is administered and localizes at the metastasized cell. Upon contact with etoposidephosphate (the prodrug), the etoposidephosphate is converted to etoposide, a chemotherapeutic drug which is taken up by the cancer cell.

Radiosensitizing agents are substances that increase the sensitivity of cells to radiation. Examples of radiosensitizing agents include nitroimidazoles, metronidazole and misonidazole (see: DeVita, V. T. Jr. in Harrison's *Principles of Internal Medicine*, p.68, McGraw-Hill Book Co., N.Y. 1983, which is incorporated herein by reference). The conjugated compound that comprises a radiosensitizing agent as the active moiety is administered and localizes at the metastasized cell. Upon exposure of the individual to radiation, the radiosensitizing agent is "excited" and causes the death of the cell.

Radionuclides may be used in pharmaceutical compositions that are useful for radiotherapy or imaging procedures.

Examples of radionuclides useful as toxins in radiation therapy include: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$B. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. Some preferred radionuclides include: 90Y, 131I $^{211}$At and $^{212}$Pb/$^{212}$Bi.

According to the present invention, the active moieties may be an imaging agent. Imaging agents are useful diagnostic procedures as well as the procedures used to identify the location of metastasized cells. Imaging can be performed by many procedures well-known to those having ordinary skill in the art and the appropriate imaging agent useful in such procedures may be conjugated to an ST receptor ligand by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}$K, $^{52}$ Fe, $^{57}$Co, $^{67}$Cu, $^{67}$Ga, $^{68}$Ga, $^{77}$Br, $^{81}$Rb/$^{81M}$Kr, $^{87M}$Sr, $^{99}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

It is preferred that the conjugated compositions be non-immunogenic or immunogenic at a very low level. Accordingly, it is preferred that the ST receptor binding moiety be a small, poorly immunogenic or non-immunogenic peptide or a non-peptide. Likewise, it is preferred that the active moiety be a small, poorly-immunogenic or non-immunogenic peptide or a non-peptide. Native ST, being a small peptide, has been shown to poorly immunogenic. (See: Klipstein, F. A. et al. (1982) *Infect. Immun.* 37:550–557; Giannella, R. A. et al. (1981) *Infect. Immun.* 33:186; Burgess, M. N. et al. (1978) *Infect. Immun.* 21:60; Evans, D. G. et al. (1973) *Infect. Immun.* 7:873; Gyles, C. L. (1979) *Ann. N.Y. Acad. Sci.* 16:314; and Sack, R. B. (1975) *Ann. Rev. Microbiol.* 29:333.) Similarly, fragments and amino acid substitute derivatives of native ST are poorly immunogenic. Accordingly, conjugated compositions which include all or part of the native ST as an ST receptor binding moiety are generally poorly immunogenic to the extent that the native ST is poorly immunogenic.

ST receptor ligands are conjugated to active agents by a variety of well-known techniques readily performed without undue experimentation by those having ordinary skill in the art. The technique used to conjugate the ST receptor ligand to the active agent is dependent upon the molecular nature of the ST receptor ligand and the active agent. After the ST receptor ligand and the active agent are conjugated to form a single molecule, assays may be performed to ensure that the conjugated molecule retains the activities of the moieties. The ST receptor binding assay described above may be performed using the conjugated compound to test whether it is capable of binding to the ST receptor. Similarly, the activity of the active moiety may be tested using various assays for each respective type of active agent. Radionuclides retain there activity, i.e. their radioactivity, irrespective of conjugation. With respect to active agents which are toxins, drugs and targeting agents, standard assays to demonstrate the activity of unconjugated forms of these compounds may be used to confirm that the activity has been retained.

Conjugation may be accomplished directly between the ST receptor ligand and the active agent or linking, intermediate molecular groups may be provided between the ST receptor ligand and the active agent. Crosslinkers are particularly useful to facilitate conjugation by providing attachment sites for each moiety. Crosslinkers may include additional molecular groups which serve as spacers to separate the moieties from each other to prevent either from interfering with the activity of the other.

In some preferred embodiments, the ST receptor ligand peptide is SEQ ID NO:2, SEQ ID NO:3, SEQ ID NOS:5–54 or fragments or derivatives thereof. It has been observed that conjugation to these molecules is preferably performed at the amino terminus of each respective peptide. In ST receptor ligand peptides comprising D amino acid sequences in the opposite order as SEQ ID NO:2, SEQ ID NO:3, SEQ ID NOS:5–54, conjugation preferably is performed at the carboxy terminus.

One having ordinary skill in the art may conjugate an ST receptor ligand peptide to a chemotherapeutic drug using well-known techniques. For example, Magerstadt, *M. Antibody Conjugates and Malignant Disease.* (1991) CRC Press, Boca Raton, USA, pp. 110–152) which is incorporated herein by reference, teaches the conjugation of various cytostatic drugs to amino acids of antibodies. Such reactions may be applied to conjugate chemotherapeutic drugs to ST receptor ligands, including ST receptor binding peptides, with an appropriate linker. ST receptor ligands which have a free amino group such as ST receptor binding peptides may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of ST. For example, one procedure for crosslinking ST receptor ligands which have a free amino group such as ST receptor binding peptides, as for example SEQ ID NO:2, SEQ ID NO:3, SEQ ID NO:5–54 to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis (sulfosuccinimidylpropionate; Pierce Co.).

In order to conjugate an ST receptor ligand peptide to a peptide-based active agent such as a toxin, the ST receptor ligand and the toxin may be produced as a single, fusion protein either by standard peptide synthesis or recombinant DNA technology, both of which can be routinely performed by those having ordinary skill in the art. Alternatively, two peptides, the ST receptor ligand peptide and the peptide-based toxin may be produced and/or isolated as separate peptides and conjugated using crosslinkers. As with conjugated compositions that contain chemotherapeutic drugs, conjugation of ST receptor binding peptides and toxins can exploit the ability to modify the single free amino group of an ST receptor binding peptide while preserving the receptor-binding function of this molecule.

One having ordinary skill in the art may conjugate an ST receptor ligand peptide to a radionuclide using well-known techniques. For example, Magerstadt, M. (1991) *Antibody Conjugates And Malignant Disease*, CRC Press, Boca Raton, Fla.,; and Barchel, S. W. and Rhodes, B. H., (1983) *Radioimaging and Radiotherapy*, Elsevier, NY, N.Y., each of which is incorporated herein by reference, teach the conjugation of various therapeutic and diagnostic radionuclides to amino acids of antibodies. Such reactions may be applied to conjugate radionuclides to ST receptor ligand peptides or to ST receptor ligands including ST receptor ligand peptides with an appropriate linker.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

The dosage administered varies depending upon factors such as: the nature of the active moiety; the nature of the conjugated composition; pharmacodynamic characteristics; its mode and route of administration; age, health, and weight of the recipient; nature and extent of symptoms; kind of concurrent treatment; and frequency of treatment.

Because conjugated compounds are specifically targeted to cells with ST receptors, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active moiety than the dosage of chemotherapeutics or toxins administered as unconjugated active agents. To determine the appropriate dose, the amount of compound is preferably measured in moles instead of by weight. In that way, the variable weight of different ST binding moieties does not affect the calculation. Presuming a one to one ratio of ST binding moiety to active moiety in conjugated compositions of the invention, less moles of conjugated compounds may be administered as compared to the moles of unconjugated compounds administered, preferably up to 100 times less moles.

Typically, chemotherapeutic conjugates are administered intravenously in multiple divided doses.

Up to 20 gm IV/dose of methotrexate is typically administered in an unconjugated form. When methotrexate is administered as the active moiety in a conjugated compound of the invention, there is a 10-to 100-fold dose reduction. Thus, presuming each conjugated compound includes one molecule of methotrexate conjugated to one ST receptor binding moiety, of the total amount of conjugated compound administered, up to about 0.2–2.0 g of methotrexate is present and therefore administered. In some embodiments, of the total amount of conjugated compound administered, up to about 200 mg–2 g of methotrexate is present and therefore administered.

Methotrexate has a molecular weight of 455. One mole of the ST peptide-methotrexate conjugate weighs between about 1755–2955 depending on the ST peptide used. The effective dose range for ST peptide-methotrexate conjugate is between about 10 to 1000 mg. In some embodiments, dosages of 50 to 500 mg of ST peptide-methotrexate conjugate are administered. In some embodiments, dosages of 80 to 240 mg of ST peptide-methotrexate conjugate are administered.

Doxorubicin and daunorubicin each weigh about 535. Thus, ST peptide-doxorubicin conjugates and ST peptide-daunorubicin conjugates each have molecular weights of between about 1835–2553.5. Presuming each conjugated compound includes one molecule of doxorubicin or daunorubicin conjugated to one ST receptor binding moiety, the effective dose range for ST peptide-doxorubicin conjugate or ST peptide-daunorubicin conjugate is between about 40 to 4000 mg. In some embodiments, dosages of 100 to 1000 mg of ST peptide-doxorubicin conjugate or ST peptide-daunorubicin conjugate are administered. In some embodiments, dosages of 200 to 600 mg of ST peptide-doxorubicin conjugate or ST peptide-daunorubicin conjugate are administered.

Toxin-containing conjugated compounds are formulated for intravenous administration. Using this approach, up to 6 nanomoles/kg of body weight of toxin have been administered as a single dose with marked therapeutic effects in patients with melanoma (Spitler L. E., et al. (1987) *Cancer Res.* 47:1717). In some embodiments, up to about 11 micrograms of ST peptide-toxin conjugated compound/kg of body weight may be administered for therapy.

Presuming each conjugated compound includes one molecule of ricin toxin A chain conjugated to an ST receptor binding moiety, conjugated compositions comprising ricin toxin A chain are administered in doses in which the proportion by weight of ricin toxin A chain is 1–500 µg of the total weight of the conjugated compound administered. In some preferred embodiments, conjugated compositions comprising ricin toxin A chain are administered in doses in which the proportion by weight of ricin toxin A chain is 10–100 µg of the total weight of the conjugated compound administered. In some preferred embodiments, conjugated compositions comprising ricin toxin A chain are administered in doses in which the proportion by weight of ricin toxin A chain is 2–50 µg of the total weight of the conjugated compound administered. The molecular weight of ricin toxin A chain is 32,000. Thus, a conjugated compound that contains ricin A chain linked to an ST peptide has a molecular weight of about 33,300–34,500. The range of doses of such conjugated compounds to be administered are 1 to 500 µg. In some embodiments, 10 to 100 µg of such conjugated compounds are administered. In some embodiments, 20 to 50 µg of such conjugated compounds are administered.

Presuming each conjugated compound includes one molecule of diphtheria toxin A chain conjugated to an ST receptor binding moiety, conjugated compositions comprising diphtheria toxin A chain are administered in doses in which the proportion by weight of diphtheria toxin A chain is 1–500 µg of the total weight of the conjugated compound administered. In some preferred embodiments, conjugated compositions comprising diphtheria toxin A chain are administered in doses in which the proportion by weight of diphtheria toxin A chain is 10–100 µg of the total weight of the conjugated compound administered. In some preferred embodiments, conjugated compositions comprising diphtheria toxin A chain are administered in doses in which the proportion by weight of diphtheria toxin A chain is 40–80 µg of the total weight of the conjugated compound administered. The molecular weight of diphtheria toxin A chain is 66,600. Thus, a conjugated compound that contains diphtheria A chain linked to an ST peptide has a molecular weight of about 67,900–69,100. The range of doses of such conjugated compounds to be administered tested are 1 to 500 µg. In some embodiments, 10 to 100 µg of such conjugated compounds are administered. In some embodiments, 40 to 80 µg of such conjugated compounds are administered.

Presuming each conjugated compound includes one molecule of Pseudomonas exotoxin conjugated to an ST receptor binding moiety, conjugated compositions comprising Pseudomonas exotoxin are administered in doses in which the proportion by weight of Pseudomonas exotoxin is 0.01–100 µg of the total weight of the conjugated compound administered. In some preferred embodiments, conjugated compositions comprising Pseudomonas exotoxin are administered in doses in which the proportion by weight of Pseudomonas exotoxin is 0.1–10 µg of the total weight of the conjugated compound administered. In some preferred embodiments, conjugated compositions comprising Pseudomonas exotoxin are administered in doses in which the proportion by weight of Pseudomonas exotoxin is 0.3–2.2 µg of the total weight of the conjugated compound administered. The molecular weight of Pseudomonas exotoxin is 22,000. Thus, a conjugated compound that contains Pseudomonas exotoxin linked to an ST peptide has a molecular weight of about 23,300–24,500. The range of doses of such conjugated compounds to be administered tested are 0.01 to 100 µg. In some embodiments, 0.1 to 10 µg of such conjugated compounds are administered. In some embodiments, 0.3 to 2.2 µg of such conjugated compounds are administered.

To dose conjugated compositions comprising ST receptor binding moieties linked to active moieties that are radioisotopes in pharmaceutical compositions useful as imaging agents, it is presumed that each ST receptor binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1–100 millicuries per dose of imaging agent, preferably 1–10 millicuries, most often 2–5 millicuries are administered. Thus, pharmaceutical compositions according to the present invention useful as imaging agents which comprise conjugated compositions comprising an ST receptor binding moiety and a radioactive moiety comprise 0.1–100 millicuries, in some embodiments preferably 1–10 millicuries, in some embodiments preferably 2–5 millicuries, in some embodiments more preferably 1–5 millicuries. Examples of dosages include: 131I=between about 0.1–100 millicuries per dose, in some embodiments preferably 1–10 millicuries, in some embodiments 2–5 millicuries, and in some embodiments about 4 millicuries; $^{111}$In=between about 0.1–100 millicuries per dose, in some embodiments preferably 1–10 millicuries, in some embodiments 1–5 millicuries, and in some embodiments about 2 millicuries; $^{99m}$Tc=between about 0.1–100 millicuries per dose, in some embodiments preferably 5–75 millicuries, in some embodiments 10–50 millicuries, and in some embodiments about 27 millicuries. Depending upon the specific activity of the radioactive moiety and the weight of the ST receptor binding moiety the dosage defined by weight varies. ST peptides have molecular weights of between about 1300–2500. In the pharmaceutical composition comprising an ST peptide linked to a single 131I in which the specific activity of $^{131}$I-ST peptide is about 2000 Ci/mmol, administering the dose of 0.1–100 millicuries is the equivalent of 0.1–100 µg $^{131}$I-ST peptide, administering the dose of 1–10 millicuries is the equivalent of 1–10 µg of $^{131}$I-ST peptide, administering the dose of 2–5 millicuries is equivalent to giving 2–5 µg of $^{131}$I-ST peptide and administering the dose of 1–5 millicuries is equivalent to giving 1–5 µg of $^{131}$I-ST peptide. In the pharmaceutical composition comprising an ST peptide linked to a single $^{111}$In in which the specific activity of $^{111}$In-ST peptide is about 1 Ci/mmol, administering the dose of 0.1–100 millicuries is the equivalent of 0.2–200 mg $^{111}$In-ST peptide, administering the dose of 1–10 millicuries is the equivalent of 2–20 mg of $^{111}$In-ST peptide, administering the dose of 2–5 millicuries is equivalent to giving 4–10 mg of $^{111}$In-ST peptide and administering the dose of 1–5 millicuries is equivalent to giving 2–10 mg of $^{111}$In-ST peptide.

To dose conjugated compositions comprising ST receptor binding moieties linked to active moieties that are radioisotopes in pharmaceutical compositions useful as therapeutic agents, it is presumed that each ST receptor binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. For therapeutics that comprise $^{131}$I, between 10–1000 nM, preferably 50–500, more preferably about 300 nanomoles of 131I at the tumor, per gram of tumor, is desirable. Thus, if there is about 1 gram of tumor, and about 0.1% of the administered dose binds to the tumor, 0.5–100 mg of $^{131}$-ST peptide conjugated compound is administered. In some embodiments, 1 to 50 mg of $^{131}$I-ST peptide conjugated compound is administered. In some embodiments, 5 to 10 mg of $^{131}$-I-ST peptide conjugated compound is administered. Wessels B. W. and R. D. Rogus (1984) Med. Phys. 11:638 and Kwok, C. S. et al. (1985) Med. Phys. 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises an ST receptor binding moiety and an active moiety wherein the active moiety is a radiostable therapeutic agent. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is selected from the group consisting of: SEQ ID NO:2, SEQ ID NO:3, SEQ ID NOS:5–54 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radiostable therapeutic agent. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–54 and fragments and derivatives thereof and the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. In some embodiments of the present invention, the pharmaceutical composition comprises a pharmaceutically acceptable carrier or diluent and a conjugated compound that comprises an ST receptor binding moiety and an active moiety wherein the active moiety is a radiostable active agent selected from the group consisting of: methotrexate, doxorubicin, daunorubicin, cytosinarabinoside, cis-platin, vindesine, mitomycin and bleomycin, alkaline phosphatase, ricin A chain, Pseudomonas exotoxin and diphtheria toxin. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radiostable active agent selected from the group consisting of: methotrexate, doxorubicin, daunorubicin, cytosinarabinoside, cis-platin, vindesine, mitomycin and bleomycin, alkaline phosphatase, ricin A. chain, Pseudomonas exotoxin and diphtheria toxin. In some embodiments of the present invention, the pharmaceutical composition comprises a pharmaceutically acceptable carrier or diluent and a radiostable conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises an ST receptor binding moiety and an active moiety wherein the active moiety is a radioactive. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NOS:5–54 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$pt and $^{197}$Hg. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–54 and fragments and derivatives thereof and the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, 131Cs, $^{143}$Pr, $^{161}$Tb, $^{177}$Lu, 191Os, $^{193M}$Pt , $^{197}$Hg, $^{32}$P and $^{33}$P, $^{71}$Ge , $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au , $^{211}$At , $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au , $^{211}$At , $^{212}$Pb, $^{212}$B , $^{32}$P and $^{33}$P, $^{71}$Ge , $^{77}$As, $^{103}$Pb, $^{105}$Rh, $^{111}$Ag, $^{119}$Sb , $^{121}$Sn, $^{131}$Cs, $^{143}$Pr, $^{161}$Tb, $^{177}$Lu, $^{191}$Os, $^{193M}$Pt and $^{197}$Hg. In some embodiments of the present invention, the pharmaceutical composition comprises a pharmaceutically acceptable carrier or diluent and a radioactive conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of detecting metastasized colorectal cancer cells in an individual suspected of suffering from metastasized colorectal cancer by radioimaging. Such individuals may be diagnosed as suffering from metastasized colorectal cancer and the metastasized colorectal cancer cells may be detected by administering to the individual, preferably by intravenous administration, a pharmaceutical composition that comprises a pharmaceutically acceptable carrier or diluent and a conjugated compound that comprises an ST receptor binding moiety and an active moiety wherein the active moiety is a radioactive and detecting the presence of a localized accumulation or aggregation of radioactivity, indicating the presence of cells with ST receptors. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is a peptide. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NOS:5–54 and fragments and derivatives thereof. In some embodiments of the present invention, the pharmaceutical composition comprises a pharmaceutically acceptable carrier or diluent and a conjugated compound that comprises an ST receptor binding moiety and an active moiety wherein the active moiety is a radioactive and the ST receptor binding moiety is selected from the group consisting of: SEQ ID NO:2, SEQ ID NO:3, SEQ ID NO:5, SEQ ID NO:6 and SEQ ID NO:54. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NOS:5–54 and fragments and derivatives thereof and the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc $^{113}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi In some embodiments of the present invention, the pharmaceutical composition comprises a pharmaceutically acceptable carrier or diluent and a conjugated compound that comprises an ST receptor binding moiety and an active moiety wherein the ST receptor binding moiety is selected from the group consisting of: SEQ ID NO:2, SEQ ID NO:3, SEQ ID NO:5, SEQ ID NO:6 and SEQ ID NO:54 and the active moiety is a radioactive agent selected from the group consisting of: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi. In some embodiments of the present invention, the pharmaceutical composition comprises a pharmaceutically acceptable carrier or diluent and a radioactive conjugated compound described in Example 1. The individual being treated may be diagnosed as having metastasized colorectal cancer or may be diagnosed as having localized colorectal cancer and may undergo the treatment proactively in the event that there is some metastasis as yet undetected. The pharmaceutical composition contains a diagnostically effective amount of the conjugated composition. A diagnostically effective amount is an amount which can be detected at a site in the body where cells with ST receptors are located without causing lethal side effects on the individual.

Another aspect of the invention relates to unconjugated compositions which comprise an ST receptor binding ligand and an active agent. For example, liposomes are small vesicles composed of lipids. Drugs can be introduced into the center of these vesicles. The outer shell of these vesicles comprise an ST receptor binding ligand. Liposomes Volumes 1, 2 and 3 CRC Press Inc. Boca Raton Fla., which is incorporated herein by reference, disclose preparation of liposome-encapsulated active agents which include targeting agents that correspond to ST receptor ligand in the outer shell. Unconjugated compositions which comprise an ST receptor ligand in the matrix of a liposome with an active agent inside include such compositions in which the ST receptor ligand is selected from the group consisting of: SEQ ID NO:2, SEQ ID NO:3, SEQ ID NOS:5–54 and fragments and derivatives thereof and the active agent is selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole.

Another aspect of the invention relates to unconjugated and conjugated compositions which comprise an ST receptor ligand used to deliver therapeutic nucleic acid molecules to cells that comprise an ST receptor such as normal cells of the intestinal tract as well as metastasized colorectal cancer cells. In some embodiments, the genetic material is delivered to metastasized tumor cells to produce an antigen that can be targeted by the immune system or to produce a protein which kills the cell or inhibits its proliferation. In some embodiments, the ST receptor ligand is used to deliver nucleic acids that encode nucleic acid molecules which replace defective endogenous genes or which encode therapeutic proteins. In some embodiments, the ST receptor ligand is thus used to deliver the active agent specifically to the cells lining the intestinal tract to treat diseases specific to this organ. According to this aspect of the invention, compositions comprise nucleic acid molecules which can replace defective genes. In some embodiments, the compositions are used in gene therapy protocols to deliver to individuals, genetic material needed and/or desired to make up for a genetic deficiency.

In some embodiments, the ST receptor ligand is combined with or incorporated into a delivery vehicle thereby converting the delivery vehicle into a specifically targeted delivery vehicle. For example, an ST receptor binding peptide may be integrated into the outer portion of a viral particle making such a virus an ST receptor-bearing cell specific virus. Similarly, the coat protein of a virus may be engineered such that it is produced as a fusion protein which includes an active ST receptor binding peptide that is exposed or otherwise accessible on the outside of the viral particle making such a virus an ST receptor-bearing cell-specific virus. In some embodiments, an ST receptor ligand may be integrated or otherwise incorporated into the liposomes wherein the ST receptor ligand is exposed or otherwise accessible on the outside of the liposome making such liposomes specifically targeted to ST receptor-bearing cells.

The active agent in the conjugated or unconjugated compositions according to this aspect of the invention is a nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposomes are small vesicles composed of lipids. Genetic constructs which encode proteins that are desired to be expressed in ST receptor-bearing cells are introduced into the center of these vesicles. The outer shell of these vesicles comprise an ST receptor ligand, in some embodiments preferably an ST peptide. Liposomes Volumes 1, 2 and 3 CRC Press Inc. Boca Raton Fla., which is incorporated herein by reference, disclose preparation of liposome-encapsulated active agents which include antibodies in the outer shell. In the present invention, an ST receptor ligand such as for example an ST peptide corresponds to the antibodies in the outer shell. Unconjugated compositions which comprise an ST receptor ligand in the matrix of a liposome with an active agent inside include such compositions in which the ST receptor ligand is selected from the group consisting of: SEQ ID NO:2, SEQ ID NO:3, SEQ ID NOS:5–54 and fragments and derivatives thereof.

In one embodiment for example, cystic fibrosis, a genetic disease in which there is a mutation of a specific gene encoding a chloride transport protein which ultimately produces abnormalities of function in many systems, most notably in the respiratory and intestinal tract, is treated by gene therapy techniques using ST receptor ligands to deliver the corrective gene to cells. Current therapy has been directed at replacing the mutant gene in the respiratory system with the normal gene by targeting these genes directly to the cells lining the respiratory tract using viruses which bind only to those cells. Similarly, the normal gene is packaged in liposomes targeted on their surface with ST receptor ligands and delivered to the intestinal tract. ST receptor ligands specifically target and direct the liposomes containing the normal gene to correct the lesion for cystic fibrosis to the specific cells lining the intestinal tract, from the duodenum to the rectum. Uptake of that genetic material by those cells should result in a cure of cystic fibrosis in th intestinal tract.

In another embodiment, the delivery of normal copies of the p53 tumor suppressor gene to the intestinal tract is accomplished using ST receptor ligand to target the gene therapeutic. Mutations of the p53 tumor suppressor gene appears to play a prominent role in th development of colorectal cancer in the intestinal tract. One approach to combatting this disease is the delivery of normal copies of this gene to the intestinal tract to cells expressing mutant forms of this gene. Genetic constructs that comprise normal p53 tumor suppressor genes are incorporated into liposomes that comprise an ST receptor ligand. The composition is delivered to the intestinal tract. ST receptor binding ligands specifically target and direct the liposomes containing the normal gene to correct the lesion created by mutation of p53 suppressor gene in intestinal cells.

Preparation of genetic constructs is with the skill of those having ordinary skill in the art. The present invention allows such construct to be specifically targeted by using the ST receptor ligands of the present invention. The compositions of the invention include an ST receptor ligand such as an ST peptide associated with a delivery vehicle and a gene construct which comprises a coding sequence for a protein whose production is desired in the cells of the intestinal tract linked to necessary regulatory sequences for expression in the cells. For uptake by cells of the intestinal tract, the compositions are administered orally or by enema whereby they enter the intestinal tract and contact cells which comprise ST receptors. The delivery vehicles associate with the ST receptor by virtue of the ST receptor ligand and the vehicle is internalized into the cell or the active agent/genetic construct is otherwise taken up by the cell. Once internalized, the construct can provide a therapeutic effect on the individual. One having ordinary skill in the art can readily formulate such compositions for oral or enema administration and determine the effective amount of such composition to be administered to treat the disease or disorder.

In addition to imaging and therapeutic compositions, systems, methods and kits, the present invention relates to methods, compositions, kits and methods useful in the in vitro screening, diagnosis and analysis of patient and patient samples. The compositions, kits and methods of the invention useful for in vitro screening, diagnosis and analysis of patient and patient samples can be used to detect ST receptor protein expression in cells wherein the presence of cells that express ST receptor is indicative of metastasis of colorectal cancer. Furthermore, the present invention relates to methods, compositions and kits useful in the in vitro screening, diagnosis and analysis of patient and patient samples to detect ST receptor protein expression in cells wherein the presence of cells that express ST receptor indicates and/or confirms that a tumor is of colorectal cancer origin. In an additional aspect of the invention, compositions, kits and methods are provided which are useful to visualize colorectal cells. Such compositions, kits and methods of analyzing tissue samples from the colon tissue to evaluate the extent of metastasis or invasion of colorectal tumor cells into the lamina propria.

In vitro screening and diagnostic compositions, methods and kits can be used in the monitoring of individuals who are in high risk groups for colorectal cancer such as those who have been diagnosed with localized disease and/or metastasized disease and/or those who are genetically linked to the disease. In vitro screening and diagnostic compositions, methods and kits can be used in the monitoring of individuals who are undergoing and/or have been treated for localized colorectal cancer to determine if the cancer has metastasized. In vitro screening and diagnostic compositions, methods and kits can be used in the monitoring of individuals who are undergoing and/or have been treated for metastasized colorectal cancer to determine if the metastasized cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing colorectal cancer. Using family health histories and/or genetic screening, it is possible to estimate the probability that a particular individual has for developing certain types of cancer including colorectal cancer. Those individuals that have been identified as being predisposed to developing a particular form of cancer can be monitored or screened to detect evidence of metastasized colorectal cancer. Upon discovery of such evidence, early treatment can be undertaken to combat the disease. Accordingly, individuals who are at risk for developing metastasized colorectal cancer may be identified and samples may be isolated form such individuals. The invention is particularly useful for monitoring individuals who have been identified as having family medical histories which include relatives who have suffered from colorectal cancer. Likewise, the invention is particularly useful to monitor individuals who have been diagnosed as having colorectal cancer and, particularly those who have been treated and had tumors removed and/or are otherwise experiencing remission including those who have been treated for metastasized colorectal cancer.

In vitro screening and diagnostic compositions, methods and kits can be used in the analysis of tumors. Expression of ST receptor is a marker for cell type and allows for the identification of the origin of adenocarcinoma of unconfirmed origin as colorectal tumors as well as allowing for an initial diagnosis of colorectal cancer to be confirmed. Tumors believed to be colorectal in origin can be confirmed as such using the compositions, methods and kits of the invention. The invention can be used to confirm the diagnosis of colorectal cancer by confirming that tumors are of colorectal origin. Similarly, tumors of unknown origin can be analyzed and identified as being colorectal in origin using the compositions, methods and kits of the invention. The invention can be used to identify colorectal tumors in samples of tumors removed from individuals suffering from adenocarcinomas of unconfirmed origin.

In vitro screening and diagnostic compositions, kits and methods of the invention can be used to analyze tissue samples from the colon tissue to evaluate the extent of metastasis or invasion of colorectal tumor cells into the lamina propria. The lamina propria represents the barrier between the colorectal tract and the rest of the body; see

*Bailey's Textbook of Histology*, 16th edition, Coperhaven et al. 1975 Williams and Wilkens, Baltimore Md. at page 404 which is incorporated herein by reference. By identifying the presence of ST receptor or mRNA that encodes ST receptor protein in cells of the lamina propria, the extent of invasion/infiltration of colorectal tumor cells into non-colorectal tissue can be evaluated and confirmed.

According to the invention, compounds are provided which bind to ST receptor protein or mRNA encoding the receptor. Normal tissue in the body does not have ST receptors or mRNA encoding ST receptors except cells of the intestinal tract. Metastasized colorectal cells may be identified by detecting in non-colorectal samples ST receptors or mRNA encoding ST receptors. The expression of ST receptor is a marker for cell type and allows for the identification of colorectal metastasis in extra-intestinal samples. ST receptor protein or mRNA encoding it may be used to visualize colorectal derived cells from other cells of the lumen in order to evaluate the level of invasion of colorectal tumor cells into the basement membrane.

In some embodiments of the invention, non-colorectal tissue and fluid samples or tumor samples may be screened to identify the presence or absence of the ST receptor protein. Techniques such as an ST receptor/ligand binding assays, ELISA assays and Western blots may be performed to determine whether the ST receptor is present in a sample.

In some embodiments of the invention, non-colorectal tissue and fluid samples or tumor samples may be screened to identify whether ST receptor protein is being expressed in cells outside of the colorectal tract by detecting the presence or absence of mRNA that encodes the ST receptor protein. The presence of mRNA that encodes the ST receptor protein or cDNA generated therefrom can be determined using techniques such as PCR amplification, Northern Blots (mRNA), Southern Blots (cDNA), or oligonucleotide hybridization.

In some embodiments of the invention, cells of non-colorectal tissue samples or tumor samples may be examined to identify the presence or absence of the ST receptor protein. Techniques such as an ST receptor/ligand binding or immunohistochemistry blots may be performed on tissue sections to determine whether the ST receptor is present in a sample.

In some embodiments of the invention, cells of non-colorectal tissue samples or tumor samples may be examined to determine whether ST receptor protein is being expressed in cells outside of the colorectal tract by detecting the presence or absence of mRNA that encodes the ST receptor protein. The presence of mRNA that encodes the ST receptor protein or cDNA generated therefrom in cells from tissue sections can be determined using techniques such as in situ hybridization.

The presence of ST receptor in non-colorectal tissue and fluid samples or on cells from non-colorectal tissue samples indicates colorectal tumor metastasis. The presence of ST receptor in a tumor sample or on tumor cells indicates that the tumor is colorectal in origin. The presence of mRNA that encodes ST receptor in non-colorectal tissue and fluid samples or in cells from non-colorectal tissue samples indicates colorectal tumor metastasis. The presence of mRNA that encodes ST receptor in tumor samples and tumor cells indicates that the tumor is colorectal in origin.

Some aspects of the present invention relate to methods and kits are provided for evaluating the metastatic migration of tumor cells in the lamina propria, indicating the level of invasion of colorectal tumor cells into the basement membrane. In some embodiments of the invention, tissue samples which include sections of the lamina propria may be isolated from individuals undergoing or recovery from surgery to remove colorectal tumors. The tissue is analyzed to determine the extent of invasion into the basement membrane of the lamina propria by neoplastic colorectal cells. Identification of the presence or absence of the ST receptor protein confirms evaluation of the migration of tumor cells into the basement membrane indicating metastasis. Techniques such as an ST receptor/ligand binding and immunohistochemistry assays may be performed to determine whether the ST receptor is present in cells in the tissue sample which are indicative of metastatic migration. Alternatively, in some embodiments of the invention, tissue samples that include the lamina propria are analyzed to identify whether ST receptor protein is being expressed in cells in the tissue sample which indicate metastatic migration by detecting the presence or absence of mRNA that encodes the ST receptor protein. The presence of mRNA that encodes the ST receptor protein or cDNA generated therefrom can be determined using techniques such as in situ hybridization.

Samples from tumors may be identified as colorectal in origin by identification of expression of ST receptors using the methods of the invention. Samples of tumors removed from individuals suffering from adenocarcinomas of unconfirmed origin can be tested to determine whether or not they possess ST receptor protein or mRNA encoding ST receptor protein. If the sample is removed from the intestinal tract, a section of frozen cells can be examined to determine if the tumor cells express ST receptor protein. If the sample is removed from the extra-intestinal tissue, a section of frozen cells can be examined to determine if the tumor cells express ST receptor protein or the sample can be homogenized and tested since the non-cancer cells will not possess ST receptor and therefore not present background.

Samples may be obtained from resected tissue or biopsy material including needle biopsy. Tissue section preparation for surgical pathology may be frozen and prepared using standard techniques. In ST binding assays on tissue sections, ST is added before fixing cells. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body such as blood, urine, lymph fluid, cerebral spinal fluid, amniotic fluid, vaginal fluid, semen and stool samples may also be screened to determine if such tumors are colorectal in origin.

Non-colorectal tissue samples may be obtained from any tissue except those of the colorectal tract, i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The cells of all tissue except those of the colorectal tract do not express the ST receptor. Thus if the ST receptor protein or mRNA encoding the ST receptor protein are detected in non-colorectal samples, the presence of metastatic colorectal cancer cells is indicated. In some preferred embodiments, the tissue samples are lymph nodes.

Tissue samples may be obtained by standard surgical techniques including use of biopsy needles. One skilled in the art would readily appreciate the variety of test samples that may be examined for ST receptor protein and recognize methods of obtaining tissue samples.

Tissue samples may be homogenized or otherwise prepared for screening for the presence of ST receptor protein by well known techniques such as sonication, mechanical disruption, chemical lysis such as detergent lysis or combinations thereof.

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for ST receptor protein. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for St receptor protein including truncated protein which is released into the blood when the ST receptor protein is cleaved from or sloughed off from metastasized colorectal tumor cells. In some embodiments, blood cell fractions are screened for the presence of metastasized colorectal tumor cells. In some embodiments, lymphocytes present in the blood cell fraction are screened by lysing the cells and detecting the presence of ST receptor protein or mENA encoding ST receptor protein which may be present as a result of the presence of any metastasized colorectal tumor cells that may have been engulfed by the blood cell.

For aspects of the invention related to analysis of lumen tissue, the invention is useful to evaluate the level of metastatic migration of colorectal tumor cells using lumen samples taken from surgery patients at and near the site of the tumor. Some aspects of the invention provide methods of analyzing tissue samples which are fixed sections routinely prepared by surgical pathologists to characterize and evaluate cells. In some embodiments, the cells are from lamina propria and are analyzed to determine and evaluate the extent of metastasis of colorectal tumor cells. The lamina propria represents the barrier between the colorectal tract and the rest of the body. By identifying the presence of ST receptor or mRNA that encodes ST receptor protein in cells of the lamina propria, the extent of invasion/infiltration of colorectal tumor cells into non-colorectal tissue can be evaluated. In some embodiments, the cells are removed in a biopsy or as an adenocarcinoma of unknown origin and are analyzed to determine and evaluate the whether they are colorectal tumor cells. In some embodiments, the cells are from a tumor suspected of being colorectal in origin and the method and compositions and kits of the invention are used to confirm the identity of the origin of the tumor cells.

Samples of the lamina propria are removed during colorectal tumor removal surgery such as by resection or colonoscopy. The sample including basement membrane cells is frozen. If an ST binding assay is to be performed, the labelled ST is contacted to the frozen section and the cells are then fixed and stained. If immunohistochemistry or in situ hybridization is to be performed, the frozen section is stained and then the assay is run. Those having ordinary skill in the art can readily isolate samples which include portions of the lamina propria and fix and stain them using standard techniques. By adding the visualization provided with an ST receptor detection technique, the section can be more comprehensively analyzed and the level of invasion of neoplastic colorectal cells into the lamina propria can be determined. The present invention may be used to analyze and evaluate the extent of progression of localized colorectal tumors, that is primary or non-metastatic colorectal tumors if these have penetrated the basement membrane underlying the mucosa into the submucosa.

Immunoassay methods may be used to identify individuals suffering from colorectal cancer metastasis by detecting presence of ST receptor protein in sample of non-colorectal tissue or body fluid using antibodies which were produced in response to exposure to ST receptor protein. Moreover, immunoassay methods may be used to identify individuals suffering from colorectal cancer by detecting presence of ST receptor protein in sample of tumor using antibodies which were produced in response to exposure to ST receptor protein.

The antibodies are preferably monoclonal antibodies. The antibodies are preferably raised against ST receptor protein made in human cells. The antibodies preferably bind to an epitope on the extracellular domain of ST receptor protein. Immunoassays are well known and there design may be routinely undertaken by those having ordinary skill in the art. Those having ordinary skill in the art can produce monoclonal antibodies which specifically bind to ST receptor protein and are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include FAbs and F(Ab)2s which specifically bind to ST receptor in place of antibodies.

Briefly, the ST receptor protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the ST receptor protein, the hybridoma which produces them is cultured to produce a continuous supply of anti-St receptor protein specific antibodies., The present invention relates to antibodies which are produced in response to exposure to ST receptor protein. The antibodies are preferably monoclonal antibodies. The antibodies are preferably raised against ST receptor protein made in human cells. In some embodiments, antibodies specifically bind to the extracellular domain of ST receptor protein. In some embodiments, antibodies specifically bind to the transmembrane domain. In some embodiments, antibodies specifically bind to the cytoplasmic domain.

The means to detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of ST receptor protein in a sample.

According to some embodiments, immunoassays comprise allowing proteins in the sample to bind a solid phase support such as a plastic surface. Detectable antibodies are then added which selectively binding to either the ST receptor protein. Detection of the detectable antibody indicates the presence of ST receptor protein. The detectable antibody may be a labelled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in *Immunoassays for the 80's*, A. Voller et al., Eds., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone, Edinburgh, 1970, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of ST receptor in a test sample is anti-ST receptor antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of ST receptor protein, detectable anti-ST receptor antibodies are used. Several methods are well known for the detection of antibodies.

One method in which the antibodies can be detectably labelled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucoseoxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labelled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3$H, $^{125}$I, $^{131}$I, $^{35}$S, and $^{14}$C. Preferably $^{125}$I is the isotope. One skilled in the art would readily recognize other radioisotopes which may also be used.

It is also possible to label the antibody with a fluorescent compound. When the fluorescent-labelled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labelled using fluorescence-emitting metals such as $^{152}$Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labelled by coupling to a chemiluminescent compound. The presence of the chemiluminescent-labelled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of ST receptor protein and no ST receptor protein, respectively, are added to assays being performed in parallel with the test assay. One skilled in the art would have the necessary knowledge to perform the appropriate controls.

ST receptor protein may be produced as a reagent for positive controls routinely. One skilled in the art would appreciate the different manners in which the ST receptor protein may be produced and isolated.

An "antibody composition" refers to the antibody or antibodies required for the detection of the protein. For example, the antibody composition used for the detection of ST receptor in a test sample comprises a first antibody that binds ST receptor protein as well as a second or third detectable antibody that binds the first or second antibody, respectively.

To examine a test sample for the presence of ST receptor protein, a standard immunometric assay such as the one described below may be performed. A first anti-ST receptor protein antibody, which recognizes a specific portion of ST receptor such as the extracellular or cytoplasmic portion, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labelled anti-ST receptor antibodies, which recognize portions of ST receptor not recognized by the first antibody, are added to the wells. The plate is incubated for a period of time sufficient for binding to occur and subsequently washed with PBS to remove unbound, labelled anti-ST receptor antibody. The amount of labelled and bound anti-St receptor antibody is subsequently determined by standard techniques.

Kits which are useful for the detection of ST receptor in a test sample comprise a container comprising anti-ST receptor antibodies and a container or containers comprising controls. Controls include one control sample which does not contain ST receptor protein and/or another control sample which contained ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include solid support, buffer, and instructions for carrying out the assay. The anti-ST receptor antibodies used in the kit preferably bind to an epitope on the extracellular domain of ST receptor protein.

The immunoassay is useful for detecting ST receptor in homogenized tissue samples and body fluid samples including the plasma portion or cells in the fluid sample.

Western Blots may be used in methods of identifying individuals suffering from colorectal cancer metastasis by detecting presence of ST receptor protein in sample of non-colorectal tissue or body fluid. Western blots may also be used to detect presence of ST receptor protein in sample of tumor from an individual suffering from cancer to identify and/r confirm that the tumor is colorectal in origin. Western blots use detectable anti-ST receptor antibodies to bind to any ST receptor present in a sample and thus indicate the presence of the receptor in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-ST receptor antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of ST receptor in a test sample by Western Blot comprise a container comprising anti-ST receptor antibodies and a container or containers comprising controls. Controls include one control sample which does not contain ST receptor protein and/or another control sample which contained ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include instructions for carrying out the assay. The antibodies of the kit preferably bind to an epitope on the extracellular domain of ST receptor protein.

Western blots are useful for detecting ST receptor in homogenized tissue samples and body fluid samples including the plasma portion or cells in the fluid sample.

ST binding assays may be used in methods of identifying individuals suffering from colorectal cancer metastasis by detecting presence of ST receptor protein in sample of non-colorectal tissue or body fluid. ST binding assays may also be used in methods to detect presence of ST receptor protein in sample of tumor from an individual suffering from cancer to identify and/r confirm that the tumor is colorectal in origin. The ST receptor binding assay uses a detectable ST receptor ligand to bind to any ST receptor present and thus indicate the presence of the receptor in a sample.

In some embodiments, the ST receptor ligand may be native ST. In some embodiments, the ST receptor ligand may be an ST receptor binding peptide. In some embodiments, the ST receptor ligand may be an ST peptide.

The ST receptor binding assay, described above, can be readily performed by those having ordinary skill in the art using readily available starting materials. ST receptor binding assays may be performed a variety of ways but each essentially identify whether or not an ST receptor protein is present in a sample by determining whether or not a detectable ST receptor ligand binds to a receptor in a sample. Briefly, the assay consists of incubating a sample with a constant concentration of an ST ligand such as $1 \times 10^{-10}$ M to $5 \times 10^{-1}$ M of $^{125}$I-ST. As a control, a duplicate preparation of a sample known to contain ST receptors are incubated with a duplicate concentration of $^{125}$I-ST. Assays are incubated to equilibrium (for example 2 hours) and the sample is analyzed to determine whether or not $^{125}$I-ST is bound to material in the sample. The $^{125}$I-ST/sample is passed through a filter which is capable of allowing $^{125}$I-ST to pass through but not capable of allowing ST receptor to pass through. Thus, if ST receptor is present in the sample, it will bind the $^{125}$I-ST which will then be trapped by the filter. Detection of $^{125}$I-ST in the filter indicates the presence of ST receptor in the sample. In some preferred embodiments, the filter is Whitman GFB glass filter paper. Controls include using samples which are known to contain ST receptors, e.g. intestinal membranes from rat intestine, human intestine, T84 cells, isolated ST receptor protein or cells expressing cloned nucleotide sequence encoding ST receptor proteins.

In addition to being conjugated to $^{125}$I, ST may be detectable by binding it to other radionuclides such as $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi, $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg or by binding it to other labels such as fluorescein or enzymes. Each of the labelling means described above for detectably labelling antibodies can be adapted to label ST receptor ligands and are considered to be described as such herein.

Kits include containers comprising detectable ST receptor ligand together with containers having positive and/or negative controls, i.e. samples which contain ST receptor and samples which contain no ST receptor, respectively. The detectable ST receptor ligand is preferably labelled. The detectable ST receptor ligand is preferably radiolabelled, preferably radiolabelled with $^{125}$I. The detectable ST receptor ligand is preferably an ST receptor binding peptide. The detectable ST receptor binding peptide is preferably an ST peptide. In some preferred embodiments, the ST peptide is selected from the group consisting of: SEQ ID NO:2, SEQ ID NO:3, SEQ ID NO:5, SEQ ID NO:6 and SEQ ID NO:54. Additional components in some kits include solid support, buffer, and instructions for carrying out the assay.

The ST receptor binding assay is useful for detecting ST receptor in homogenized tissue samples and body fluid samples including the plasma portion or cells in the fluid sample.

In addition to detection of the ST receptor protein, aspects of the present invention include various methods of determining whether a sample contains cells that express ST receptor by nucleotide sequence-based molecular analysis. Several different methods are available for doing so including those using Polymerase Chain Reaction (PCR) technology, using Northern blot technology, oligonucleotide hybridization technology, and in situ hybridization technology.

The invention relates to oligonucleotide probes and primers used in the methods of identifying mRNA that encodes ST receptor and to diagnostic kits which comprise such components.

The mRNA sequence-based methods for determining whether a sample mRNA encoding ST receptor include but are not limited to polymerase chain reaction technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence of specific mRNA that encodes ST receptor in non-colorectal samples may be employed according to the invention.

A preferred method to detecting mRNA that encodes ST receptor in genetic material derived from non-colorectal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequence encoding ST receptor protein is well known such as in U.S. Pat. No. 5,237,051 and F. J. Sauvage et al. 1991 *J. Biol. Chem.* 266:17912–17918 which are incorporated herein by reference. To perform this method, RNA is extracted from cells in a sample and tested or used to make cDNA using well known methods and readily available starting materials.

Those having ordinary skill in the art can readily prepare PCR primers. A set of primers generally contains two primers. When performing PCR on extracted mRNA or cDNA generated therefrom, if the mRNA or cDNA encoding ST receptor protein is present, multiple copies of the mRNA or cDNA will be made. If it is not present, PCR will not generate a discrete detectable product. Primers are generally 8–50 nucleotides, preferably about 15–35 nucleotides, more preferably 18–28 nucleotides, which are identical or complementary to and therefor hybridize to the mRNA or cDNA generated therefrom which encodes ST receptor protein. In preferred embodiments, the primers are each 15–35 nucleotide, more preferably 18–28 nucleotide fragments of the nucleic acid molecule that comprises the nucleotide sequence encoding ST receptor protein as described in U.S. Pat. No. 5,237,051 and F. J. Sauvage et al. 1991 *J. Biol. Chem.* 266:17912–17918. The primer must hybridize to the sequence to be amplified. Typical primers are 18–28 nucleotides in length and are generally have 50% to 60% G+C composition. The entire primer is preferably complementary to the sequence it must hybridize to. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences. The extracellular domain is the most unique portion of the ST receptor protein. At least one primer hybridizes to a nucleotide sequence that corresponds to the extracellular domain of the ST receptor protein.

In some preferred embodiments, the 5' PCR primer is designed based upon nucleotides 15–41 of the ST receptor coding sequence as described in U.S. Pat. No. 5,237,051. In some preferred embodiments, the 5' PCR primer is designed based upon nucleotides 20–40 of the ST receptor coding sequence as described in U.S. Pat. No. 5,237,051. In some preferred embodiments, the 5' PCR primer is designed based upon nucleotides 25–43 of the ST receptor coding sequence as described in U.S. Pat. No. 5,237,051. In some preferred embodiments, the 5' PCR primer is designed based upon nucleotides 40–62 of the ST receptor coding sequence as described in U.S. Pat. No. 5,237,051. In some preferred embodiments, the 3' PCR primer is designed based upon nucleotides 350–375 of the ST receptor coding sequence as described in U.S. Pat. No. 5,237,051. In some preferred embodiments, the 3' PCR primer is designed based upon nucleotides 290–308 of the ST receptor coding sequence as described in U.S. Pat. No. 5,237,051. In some preferred embodiments, the 3' PCR primer is designed based upon nucleotides 121–141 of the ST receptor coding sequence as described in U.S. Pat. No. 5,237,051. In some preferred embodiments, the 3' PCR primer is designed based upon nucleotides 171–196 of the ST receptor coding sequence as described in U.S. Pat. No. 5,237,051.

The mRNA or cDNA is combined with the primers, free nucleotides and enzyme following standard PCR protocols. The mixture undergoes a series of temperature changes. If the mRNA or cDNA encoding ST receptor is present, that is, if both primers hybridize to sequences on the same molecule, the molecule comprising the primers and the intervening complementary sequences will be exponentially amplified. The amplified DNA can be easily detected by a variety of well known means. If no mRNA or cDNA that encodes ST receptor is present, no PCR product will be exponentially amplified. The PCR technology therefore provides an extremely easy, straightforward and reliable method of detecting mRNA encoding ST receptor protein in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify mRNA or cDNA that encodes ST receptor protein.

According to the invention, diagnostic kits can be assembled which are useful to practice methods of detecting the presence of mRNA or cDNA that encodes ST receptor in non-colorectal samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding ST receptor.

PCR assays are useful for detecting mRNA encoding ST receptor in homogenized tissue samples and cells in body fluid samples. It is contemplated that PCR on the plasma portion of a fluid sample could be used to detect mRNA encoding ST receptor protein.

Another method of determining whether a sample contains cells expressing ST receptor is by Northern Blot analysis of mRNA extracted from a non-colorectal sample. The techniques for performing Northern blot analyses are well known by those having ordinary skill in the art and are described in Sambrook, J. et al., (1989) *Molecular Cloning: A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper. Probes useful to identify mRNA in a Northern Blot have a nucleotide sequence that is complementary to mRNA transcribed from the gene that encodes ST receptor protein. Those having ordinary skill in the art could use the sequence information in U.S. Pat. No. 5,237,051 and F. J. Sauvage et al. 1991 *J. Biol. Chem.* 266:17912–17918 to design such probes or to isolate and clone the ST receptor gene or cDNA which can be used as a probe. Probes preferably hybridize to the portion of the mRNA that corresponds to the extracellular domain of the ST receptor protein. In preferred embodiments, the probes are full length clones or fragments of the nucleic acid molecule that comprises the nucleotide sequence encoding ST receptor protein as described in U.S. Pat. No. 5,237,051 and F. J. Sauvage et al. 1991 *J. Biol. Chem.* Such probes are at least 15 nucleotides, preferably 30–200, more preferably 40–100 nucleotide fragments and may be the entire coding sequence of ST receptors, more preferably 18–28 nucleotide fragments of the nucleic acid molecule that comprises the nucleotide sequence encoding ST receptor protein as described in U.S. Pat. No. 5,237,051 and F. J. Sauvage et al. 1991 *J. Biol. Chem.* 266:17912–17918. A preferred probe hybridizes to the mRNA that encodes ST receptor protein from nucleotide 50 to nucleotide 90.

According to the invention, diagnostic kits can be assembled which are useful to practice methods of detecting the presence of mRNA that encodes ST receptor in non-colorectal samples by Northern blot analysis. Such diagnostic kits comprise oligonucleotide which are useful as probes for hybridizing to the mRNA. The probes may be radiolabelled. It is preferred that diagnostic kits according to the present invention comprise a container comprising a size marker to be run as a standard on a gel. It is preferred that diagnostic kits according to the present invention comprise a container comprising a positive control which will hybridize to the probe.

Northern blot analysis is useful for detecting mRNA encoding ST receptor in homogenized tissue samples and cells in body fluid samples. It is contemplated that PCR on the plasma portion of a fluid sample could be used to detect mRNA encoding ST receptor protein.

Another method of detecting the presence of mRNA encoding ST receptor protein by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding ST receptor protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to ST receptor cDNA. In some preferred embodiments the probes of the invention are 30–200 nucleotides, preferably 40–100 nucleotides. The probes preferably contain a sequence that is complementary to the portion that encodes the extracellular domain of the ST receptor.

One having ordinary skill in the art, using the sequence information disclosed in U.S. Pat. No. 5,237,051 and F. J. Sauvage et al. 1991 *J. Biol. Chem.* 266:17912–17918 can design probes which are fully complementary to mRNA sequences but not genomic DNA sequences. Hybridization conditions can be routinely optimized to minimize background signal by non-fully complementary hybridization. Probes preferably hybridize to the portion of the mRNA that includes a nucleotide sequence that corresponds to the extracellular domain of the ST receptor protein. Probes preferably hybridize to the portion of the mRNA that corresponds to the extracellular domain of the ST receptor protein. In preferred embodiments, the probes are full length clones or fragments of the nucleic acid molecule that comprises the nucleotide sequence encoding ST receptor protein as described in U.S. Pat. No. 5,237,051 and F. J. Sauvage et al. 1991 *J. Biol. Chem.* Such probes are at least 15 nucleotides, preferably 30–200, more preferably 40–100 nucleotide fragments and may be the entire coding sequence of ST receptors, more preferably 18–28 nucleotide fragments of the nucleic acid molecule that comprises the nucleotide sequence encoding ST receptor protein as described in U.S. Pat. No. 30 5,237,051 and F. J. Sauvage et al. 1991 *J. Biol. Chem.* 266:17912–17918. A preferred probe hybridizes to the mRNA that encodes ST receptor protein from nucleotide 50 to nucleotide 90.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems.

According to the invention, diagnostic kits can be assembled which are useful to practice oligonucleotide hybridization methods of the invention. Such diagnostic kits comprise a labelled oligonucleotide which encodes portions of ST receptor encoded by different exons. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Those having ordinary skill in the art could use the sequence information in U.S. Pat. No. 5,237,051 and F. J. Sauvage et al. 1991 *J. Biol. Chem.* 266:17912–17918 to design such probes or to isolate and clone the ST receptor gene or cDNA which can be used as a probe. Either the coding strand or its complementary strand may be used as a probe.

Oligonucleotide hybridization techniques are useful for detecting mRNA encoding ST receptor in homogenized tissue samples and cells in body fluid samples. It is contemplated that PCR on the plasma portion of a fluid sample could be used to detect mRNA encoding ST receptor protein.

The present invention relates to in vitro kits for evaluating tissues samples to determine the level of metastasis and to reagents and compositions useful to practice the same.

In some embodiments of the invention, tissue samples that include portions of the lamina propria may be isolated from individuals undergoing or recovery from surgery to remove colorectal tumors include resection or colonoscopy. The tissue is analyzed to identify the presence or absence of the ST receptor protein. Techniques such as an ST receptor/ligand binding assays and immunohistochemistry assays may be performed to determine whether the ST receptor is present in cells in the tissue sample which are indicative of metastatic migration. Alternatively, in some embodiments of the invention, tissue samples are analyzed to identify whether ST receptor protein is being expressed in cells in the tissue sample which indicate metastatic migration by detecting the presence or absence of mRNA that encodes the ST receptor protein. The presence of mRNA that encodes the ST receptor protein or cDNA generated therefrom can be determined using techniques such as in situ hybridization, immunohistochemistry and in situ ST binding assay.

The present invention relates to in vitro kits for evaluating samples of tumors to determine whether or not they are colorectal in origin and to reagents and compositions useful to practice the same. In some embodiments of the invention, tumor samples may be isolated from individuals undergoing or recovery from surgery to remove tumors in the colon, tumors in other organs or biopsy material. The tumor sample is analyzed to identify the presence or absence of the ST receptor protein. Techniques such as an ST receptor/ligand binding assays and immunohistochemistry assays may be performed to determine whether the ST receptor is present in cells in the tumor sample which are indicative of colorectal origin. Alternatively, in some embodiments of the invention, lumen tissue samples are analyzed to identify whether ST receptor protein is being expressed in cells in the tumor sample which indicate colorectal origin by detecting the presence or absence of mRNA that encodes the ST receptor protein. The presence of mRNA that encodes the ST receptor protein or cDNA generated therefrom can be determined using techniques such as in situ hybridization, immunohistochemistry and in situ ST binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them.

Probes useful in oligonucleotide assays at least 18 nucleotides of complementary DNA and may be as large as a complete complementary sequence to ST receptor mRNA. In some preferred embodiments the probes of the invention are 30–200 nucleotides, preferably 40–100 nucleotides. The probes preferably contain a sequence that is complementary to the portion that encodes the extracellular domain of the ST receptor.

One having ordinary skill in the art, using the sequence information disclosed in U.S. Pat. No. 5,237,051 and F. J. Sauvage et al. 1991 J. Biol. Chem. 266:17912–17918 can design probes useful in in situ hybridization technology to identify cells that express ST receptor. Probes preferably hybridizes to a nucleotide sequence that corresponds to the extracellular domain of the ST receptor protein. Hybridization conditions can be routinely optimized to minimize background signal by non-fully complementary hybridization. Probes preferably hybridize to the portion of the mRNA that includes a nucleotide sequence that corresponds to the extracellular domain of the ST receptor protein. Probes preferably hybridize to the portion of the mRNA that corresponds to the extracellular domain of the ST receptor protein. In preferred embodiments, the probes are full length clones or fragments of the nucleic acid molecule that comprises the nucleotide sequence encoding ST receptor protein as described in U.S. Pat. No. 5,237,051 and F. J. Sauvage et al. 1991 J. Biol. Chem. Such probes are at least 15 nucleotides, preferably 30–200, more preferably 40–100 nucleotide fragments and may be the entire coding sequence of ST receptors, more preferably 18–28 nucleotide fragments of the nucleic acid molecule that comprises the nucleotide sequence encoding ST receptor protein as described in U.S. Pat. No. 5,237,051 and F. J. Sauvage et al. 1991 J. Biol. Chem. 266:17912–17918. A preferred probe hybridizes to the mRNA that encodes ST receptor protein from nucleotide 50 to nucleotide 90.

The probes a fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labelled with florescent but can be subsequently detected with florescent marker.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems.

The present invention relates to probes useful for in situ hybridization to identify cells that express ST receptor protein.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes portions encoded by different exons. It is preferred that labelled probes of the in situ diagnostic kits according to the present invention are labelled with a fluorescent marker.

Those having ordinary skill in the art can analyze the fixed cells to characterize the level of metastatic migration of the colon cancer cells. The labelling of colon-derived cells allows for improved analysis.

Immunohistochemistry techniques may be used to identify and essentially stain cells with ST receptor. Such "staining" allows for analysis of metastatic migration. Anti-ST receptor antibodies such as those described above of contacted with fixed cells and the ST receptor present in the cells reacts with the antibodies. The antibodies are detectably labelled or detected using labelled second antibody or protein A to stain the cells.

ST binding assays may be performed instead of immunohistochemistry except that the cell section is first frozen, then the ST binding assay is performed and then the cells are fixed.

The techniques described herein for evaluating tumor sections can also be used to analyze tissue sections for samples of lymph nodes as well as other tissues to identify the presence of colorectal tumor cells. The samples can be prepared and "stained" to detect expression of ST receptor.

The following examples are illustrative but are not meant to be limiting of the present invention.

EXAMPLES

Example 1

The following are representative compounds according to the present invention. Whenever stated below, reference to a series of compounds is provided for efficiency and is meant to name each compound in the series including all the compounds in numerical order, such as for example "3-D1 to 3-D16" is meant to refer to compounds 3-D1, 3-D2, 3-D3, 3-D4, 3-D5, 3-D6, 3-D7, 3-D8, 3-D9, 3-D10, 3-D11, 3-D12, 3-D13, 3-D14, 3-D15 and 3-D16. Likewise, whenever stated below, reference to a series of SEQ ID NO:'s is provided for efficiency and is meant to name each SEQ ID NO: in the series including the all SEQ ID NO:'s in numerical order, such as for example SEQ ID NO:5 through SEQ ID NO:54 is meant to refer to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53 and SEQ ID NO:54. Similarly, whenever stated below, reference to a series of compounds is provided for efficiency and is meant to name each compound in the series including the all compounds in numerical order, such as for example "5-AP to 54-AP" is meant to refer to compounds 5-AP, 6-AP, 7-AP, 8-AP, 9-AP, 10-AP, 11-AP, 12-AP, 13-AP, 14-AP, 15-AP, 16-AP, 17-AP, 18-AP, 19-AP, 20-AP, 21-AP, 22-AP, 23-AP, 24-AP, 25-AP, 26-AP, 27-AP, 28-AP, 29-AP, 30-AP, 31-AP, 32-AP, 33-AP, 34-AP, 35-AP, 36-AP, 37-AP, 38-AP, 39-AP, 40-AP, 41-AP, 42-AP, 43-AP, 44-AP, 45-AP, 46-AP, 47-AP, 48-AP, 49-AP, 50-AP, 51-AP, 52-AP, 53-AP and 54-AP.

Compound 2-D1 comprises methotrexate (amethopterin) conjugated to SEQ ID NO:2.

Compound 2-D2 comprises doxorubicin (adrimycin) conjugated to SEQ ID NO:2.

Compound 2-D3 comprises daunorubicin conjugated to SEQ ID NO:2.

Compound 2-D4 comprises cytosinarabinoside conjugated to SEQ ID NO:2.

Compound 2-D5 comprises etoposide conjugated to SEQ ID NO:2.

Compound 2-D6 comprises 5-4 fluorouracil conjugated to SEQ ID NO:2.

Compound 2-D7 comprises melphalan conjugated to SEQ ID NO:2.

Compound 2-D8 comprises chlorambucil conjugated to SEQ ID NO:2.

Compound 2-D9 comprises cyclophosphamide conjugated to SEQ ID NO:2.

Compound 2-D10 comprises cis-platinum conjugated to SEQ ID NO:2.

Compound 2-D11 comprises vindesine conjugated to SEQ ID NO:2.

Compound 2-D12 comprises mitomycin conjugated to SEQ ID NO:2.

Compound 2-D13 comprises bleomycin conjugated to SEQ ID NO:2.

Compound 2-D14 comprises purothionin conjugated to SEQ ID NO:2.

Compound 2-D15 comprises macromomycin conjugated to SEQ ID NO:2.

Compound 2-D16 comprises trenimon conjugated to SEQ ID NO:2.

Compounds 3-D1 to 3-D16 are the same as compounds 2-D1 to 2-D16, respectively, except instead of comprising SEQ ID NO:2 as the ST receptor binding moiety, compounds 3-D1 to 3-D16 each comprise SEQ ID NO:3 as the ST receptor binding moiety.

Compounds 5-D1 to 5-D16 are the same as compounds 2-D1 to 2-D16, respectively, except instead of comprising SEQ ID NO:2 as the ST receptor binding moiety, compounds 5-D1 to 5-D16 each comprise SEQ ID NO:5 as the ST receptor binding moiety.

Compounds 6-D1 to 6-D16 are the same as compounds 2-D1 to 2-D16, respectively, except instead of comprising SEQ ID NO:2 as the ST receptor binding moiety, compounds 6-D1 to 6-D16 each comprise SEQ ID NO:6 as the ST receptor binding moiety.

Compounds 7-D1 to 7-D16 are the same as compounds 2-D1 to 2-D16, respectively, except instead of comprising SEQ ID NO:2 as the ST receptor binding moiety, compounds 7-D1 to 7-D16 each comprise SEQ ID NO:7 as the ST receptor binding moiety.

Compounds 8-D1 to 8-D16 are the same as compounds 2-D1 to 2-D16, respectively, except instead of comprising SEQ ID NO:2 as the ST receptor binding moiety, compounds 8-D1 to 8-D16 each comprise SEQ ID NO:8 as the ST receptor binding moiety.

Compounds 9-D1 to 9-D16 are the same as compounds 2-D1 to 2-D16, respectively, except instead of comprising SEQ ID NO:2 as the ST receptor binding moiety, compounds 9-D1 to 9-D16 each comprise SEQ ID NO:9 as the ST receptor binding moiety.

Compounds 10-D1 to 10-D16 are the same as compounds 2-D1 to 2-D16, respectively, except instead of comprising SEQ ID NO:2 as the ST receptor binding moiety, compounds 10-D1 to 10-D16 each comprise SEQ ID NO:2 as the ST receptor binding moiety.

Compounds 12-D1 to 12-D16 are the same as compounds 2-D1 to 2-D16, respectively, except instead of comprising SEQ ID NO:2 as the ST receptor binding moiety, compounds 12-D1 to 12-D16 each comprise SEQ ID NO:ll as the ST receptor binding moiety.

Compounds 12-D1 to 12-D16 are the same as compounds 2-D1 to 2-D16, respectively, except instead of comprising SEQ ID NO:2 as the ST receptor binding moiety, compounds 12-D1 to 12-D16 each comprise SEQ ID NO:12 as the ST receptor binding moiety.

Compounds 13-D1 to 13-D16 are the same as compounds 2-D1 to 2-D16, respectively, except instead of comprising SEQ ID NO:2 as the ST receptor binding moiety, compounds 13-D1 to 13-D16 each comprise SEQ ID NO:13 as the ST receptor binding moiety.

Compounds 14-D1 to 14-D16 are the same as compounds 2-D1 to 2-D16, respectively, except instead of comprising SEQ ID NO:2 as the ST receptor binding moiety, compounds 14-D1 to 14-D16 each comprise SEQ ID NO:14 as the ST receptor binding moiety.

Compounds 15-D1 to 15-D16 are the same as compounds 2-D1 to 2-D16, respectively, except instead of comprising SEQ ID NO:2 as the ST receptor binding moiety, compounds 15-D1 to 15-D16 each comprise SEQ ID NO:15 as the ST receptor binding moiety.

Compounds 16-D1 to 16-D16 are the same as compounds 2-D1 to 2-D16, respectively, except instead of comprising SEQ ID NO:2 as the ST receptor binding moiety, compounds 16-D1 to 16-D16 each comprise SEQ ID NO:16 as the ST receptor binding moiety.

Compounds 17-D1 to 17-D16 are the same as compounds 2-D1 to 2-D16, respectively, except instead of comprising SEQ ID NO:2 as the ST receptor binding moiety, compounds 17-D1 to 17-D16 each comprise SEQ ID NO:17 as the ST receptor binding moiety.

Compounds 18-D1 to 18-D16 are the same as compounds 2-D1 to 2-D16, respectively, except instead of comprising SEQ ID NO:2 as the ST receptor binding moiety, compounds 18-D1 to 18-D16 each comprise SEQ ID NO:18 as the ST receptor binding moiety.

Compounds 19-D1 to 19-D16 are the same as compounds 2-D1 to 2-D16, respectively, except instead of comprising SEQ ID NO:2 as the ST receptor binding moiety, compounds 19-D1 to 19-D16 each comprise SEQ ID NO:19 as the ST receptor binding moiety.

Compounds 20-D1 to 20-D16 are the same as compounds 2-D1 to 2-D16, respectively, except instead of comprising SEQ ID NO:2 as the ST receptor binding moiety, compounds 20-D1 to 20-D16 each comprise SEQ ID NO:20 as the ST receptor binding moiety.

Compounds 22-D1 to 22-D16 are the same as compounds 2-D1 to 2-D16, respectively, except instead of comprising SEQ ID NO:2 as the ST receptor binding moiety, compounds 22-D1 to 22-D16 each comprise SEQ ID NO:21 as the ST receptor binding moiety.

Compounds 22-D1 to 22-D16 are the same as compounds 2-D1 to 2-D16, respectively, except instead of comprising SEQ ID NO:2 as the ST receptor binding moiety, compounds 22-D1 to 22-D16 each comprise SEQ ID NO:22 as the ST receptor binding moiety.

Compounds 23-D1 to 23-D16 are the same as compounds 2-D1 to 2-D16, respectively, except instead of comprising SEQ ID NO:2 as the ST receptor binding moiety, compounds 23-D1 to 23-D16 each comprise SEQ ID NO:23 as the ST receptor binding moiety.

Compounds 24-D1 to 24-D16 are the same as compounds 2-D1 to 2-D16, respectively, except instead of comprising SEQ ID NO:2 as the ST receptor binding moiety, compounds 24-D1 to 24-D16 each comprise SEQ ID NO:24 as the ST receptor binding moiety.

Compounds 25-D1 to 25-D16 are the same as compounds 2-D1 to 2-D16, respectively, except instead of comprising SEQ ID NO:2 as the ST receptor binding moiety, compounds 25-D1 to 25-D16 each comprise SEQ ID NO:25 as the ST receptor binding moiety.

Compounds 26-D1 to 26-D16 are the same as compounds 2-D1 to 2-D16, respectively, except instead of comprising SEQ ID NO:2 as the ST receptor binding moiety, compounds 26-D1 to 26-D16 each comprise SEQ ID NO:26 as the ST receptor binding moiety.

Compounds 27-D1 to 27-D16 are the same as compounds 2-D1 to 2-D16, respectively, except instead of comprising SEQ ID NO:2 as the ST receptor binding moiety, compounds 27-D1 to 27-D16 each comprise SEQ ID NO:27 as the ST receptor binding moiety.

Compounds 28-D1 to 28-D16 are the same as compounds 2-D1 to 2-D16, respectively, except instead of comprising SEQ ID NO:2 as the ST receptor binding moiety, compounds 28-D1 to 28-D16 each comprise SEQ ID NO:28 as the ST receptor binding moiety.

Compounds 29-D1 to 29-D16 are the same as compounds 2-D1 to 2-D16, respectively, except instead of comprising SEQ ID NO:2 as the ST receptor binding moiety, compounds 29-D1 to 29-D16 each comprise SEQ ID NO:29 as the ST receptor binding moiety.

Compounds 30-D1 to 30-D16 are the same as compounds 2-D1 to 2-D16, respectively, except instead of comprising SEQ ID NO:2 as the ST receptor binding moiety, compounds 30-D1 to 30-D16 each comprise SEQ ID NO:30 as the ST receptor binding moiety.

Compounds 32-D1 to 32-D16 are the same as compounds 2-D1 to 2-D16, respectively, except instead of comprising SEQ ID NO:2 as the ST receptor binding moiety, compounds 32-D1 to 32-D16 each comprise SEQ ID NO:31 as the ST receptor binding moiety.

Compounds 32-D1 to 32-D16 are the same as compounds 2-D1 to 2-D16, respectively, except instead of comprising SEQ ID NO:2 as the ST receptor binding moiety, compounds 32-D1 to 32-D16 each comprise SEQ ID NO:32 as the ST receptor binding moiety.

Compounds 33-D1 to 33-D16 are the same as compounds 2-D1 to 2-D16, respectively, except instead of comprising SEQ ID NO:2 as the ST receptor binding moiety, compounds 33-D1 to 33-D16 each comprise SEQ ID NO:33 as the ST receptor binding moiety.

Compounds 34-D1 to 34-D16 are the same as compounds 2-D1 to 2-D16, respectively, except instead of comprising SEQ ID NO:2 as the ST receptor binding moiety, compounds 34-D1 to 34-D16 each comprise SEQ ID NO:34 as the ST receptor binding moiety.

Compounds 35-D1 to 35-D16 are the same as compounds 2-D1 to 2-D16, respectively, except instead of comprising SEQ ID NO:2 as the ST receptor binding moiety, compounds 35-D1 to 35-D16 each comprise SEQ ID NO:35 as the ST receptor binding moiety.

Compounds 36-D1 to 36-D16 are the same as compounds 2-D1 to 2-D16, respectively, except instead of comprising SEQ ID NO:2 as the ST receptor binding moiety, compounds 36-D1 to 36-D16 each comprise SEQ ID NO:36 as the ST receptor binding moiety.

Compounds 37-D1 to 37-D16 are the same as compounds 2-D1 to 2-D16, respectively, except instead of comprising SEQ ID NO:2 as the ST receptor binding moiety, compounds 37-D1 to 37-D16 each comprise SEQ ID NO:37 as the ST receptor binding moiety.

Compounds 38-D1 to 38-D16 are the same as compounds 2-D1 to 2-D16, respectively, except instead of comprising SEQ ID NO:2 as the ST receptor binding moiety, compounds 38-D1 to 38-D16 each comprise SEQ ID NO:38 as the ST receptor binding moiety.

Compounds 39-D1 to 39-D16 are the same as compounds 2-D1 to 2-D16, respectively, except instead of comprising SEQ ID NO:2 as the ST receptor binding moiety, compounds 39-D1 to 39-D16 each comprise SEQ ID NO:39 as the ST receptor binding moiety.

Compounds 40-D1 to 40-D16 are the same as compounds 2-D1 to 2-D16, respectively, except instead of comprising SEQ ID NO:2 as the ST receptor binding moiety, compounds 40-D1 to 40-D16 each comprise SEQ ID NO:40 as the ST receptor binding moiety.

Compounds 42-D1 to 42-D16 are the same as compounds 2-D1 to 2-D16, respectively, except instead of comprising SEQ ID NO:2 as the ST receptor binding moiety, compounds 42-D1 to 42-D16 each comprise SEQ ID NO:41 as the ST receptor binding moiety.

Compounds 42-D1 to 42-D16 are the same as compounds 2-D1 to 2-D16, respectively, except instead of comprising SEQ ID NO:2 as the ST receptor binding moiety, compounds 42-D1 to 42-D16 each comprise SEQ ID NO:42 as the ST receptor binding moiety.

Compounds 43-D1 to 43-D16 are the same as compounds 2-D1 to 2-D16, respectively, except instead of comprising SEQ ID NO:2 as the ST receptor binding moiety, compounds 43-D1 to 43-D16 each comprise SEQ ID NO:43 as the ST receptor binding moiety.

Compounds 44-D1 to 44-D16 are the same as compounds 2-D1 to 2-D16, respectively, except instead of comprising SEQ ID NO:2 as the ST receptor binding moiety, compounds 44-D1 to 44-D16 each comprise SEQ ID NO:44 as the ST receptor binding moiety.

Compounds 45-D1 to 45-D16 are the same as compounds 2-D1 to 2-D16, respectively, except instead of comprising SEQ ID NO:2 as the ST receptor binding moiety, compounds 45-D1 to 45-D16 each comprise SEQ ID NO:45 as the ST receptor binding moiety.

Compounds 46-D1 to 46-D16 are the same as compounds 2-D1 to 2-D16, respectively, except instead of comprising SEQ ID NO:2 as the ST receptor binding moiety, compounds 46-D1 to 46-D16 each comprise SEQ ID NO:46 as the ST receptor binding moiety.

Compounds 47-D1 to 47-D16 are the same as compounds 2-D1 to 2-D16, respectively, except instead of comprising SEQ ID NO:2 as the ST receptor binding moiety, compounds 47-D1 to 47-D16 each comprise SEQ ID NO:47 as the ST receptor binding moiety.

Compounds 48-D1 to 48-D16 are the same as compounds 2-D1 to 2-D16, respectively, except instead of comprising SEQ ID NO:2 as the ST receptor binding moiety, compounds 48-D1 to 48-D16 each comprise SEQ ID NO:48 as the ST receptor binding moiety.

Compounds 49-D1 to 49-D16 are the same as compounds 2-D1 to 2-D16, respectively, except instead of comprising SEQ ID NO:2 as the ST receptor binding moiety, compounds 49-D1 to 49-D16 each comprise SEQ ID NO:49 as the ST receptor binding moiety.

Compounds 50-D1 to 50-D16 are the same as compounds 2-D1 to 2-D16, respectively, except instead of comprising SEQ ID NO:2 as the ST receptor binding moiety, compounds 50-D1 to 50-D16 each comprise SEQ ID NO:50 as the ST receptor binding moiety.

Compounds 51-D1 to 51-D16 are the same as compounds 2-D1 to 2-D16, respectively, except instead of comprising SEQ ID NO:2 as the ST receptor binding moiety, compounds 51-D1 to 51-D16 each comprise SEQ ID NO:51 as the ST receptor binding moiety.

Compounds 52-D1 to 52-D16 are the same as compounds 2-D1 to 2-D16, respectively, except instead of comprising SEQ ID NO:2 as the ST receptor binding moiety, compounds 52-D1 to 52-D16 each comprise SEQ ID NO:52 as the ST receptor binding moiety.

Compounds 53-D1 to 53-D16 are the same as compounds 2-D1 to 2-D16, respectively, except instead of comprising SEQ ID NO:2 as the ST receptor binding moiety, compounds 53-D1 to 53-D16 each comprise SEQ ID NO:53 as the ST receptor binding moiety.

Compounds 54-D1 to 54-D16 are the same as compounds 2-D1 to 2-D16, respectively, except instead of comprising SEQ ID NO:2 as the ST receptor binding moiety, compounds 54-D1 to 54-D16 each comprise SEQ ID NO:54 as the ST receptor binding moiety.

Compound 2-T1 comprises ricin conjugated to SEQ ID NO:2.

Compound 2-T2 comprises ricin A chain (ricin toxin) conjugated to SEQ ID NO:2.

Compound 2-T3 comprises Pseudomonas exotoxin (PE) conjugated to SEQ ID NO:2.

Compound 2-T4 comprises diphtheria toxin (DT), conjugated to SEQ ID NO:2.

Compound 2-T5 comprises Clostridium perfringens phospholipase C (PLC) conjugated to SEQ ID NO:2.

Compound 2-T6 comprises bovine pancreatic ribonuclease (BPR) conjugated to SEQ ID NO:2.

Compound 2-T7 comprises pokeweed antiviral protein (PAP) conjugated to SEQ ID NO:2.

Compound 2-T8 comprises abrin conjugated to SEQ ID NO:2.

Compound 2-T9 comprises abrin A chain (abrin toxin) conjugated to SEQ ID NO:2.

Compound 2-T10 comprises cobra venom factor (CVF) conjugated to SEQ ID NO:2.

Compound 2-T11 comprises gelonin (GEL) conjugated to SEQ ID NO:2.

Compound 2-T12 comprises saporin (SAP) conjugated to SEQ ID NO:2.

Compound 2-T13 comprises modeccin conjugated to SEQ ID NO:2.

Compound 2-T14 comprises viscumin conjugated to SEQ ID NO:2.

Compound 2-T15 comprises volkensin conjugated to SEQ ID NO:2.

Compounds 3-T1 to 3-T15 are the same as compounds 2-T1 to 2-T15, respectively, except instead of comprising SEQ ID NO:2 as the ST receptor binding moiety, compounds 3-T1 to 3-T15 each comprise SEQ ID NO:3 as the ST receptor binding moiety.

Compounds 5-T1 to 5-T15 are the same as compounds 2-T1 to 2-T15, respectively, except instead of comprising SEQ ID NO:2 as the ST receptor binding moiety, compounds 5-T1 to 5-T15 each comprise SEQ ID NO:5 as the ST receptor binding moiety.

Compounds 6-T1 to 6-T15 are the same as compounds 2-T1 to 2-T15, respectively, except instead of comprising SEQ ID NO:2 as the ST receptor binding moiety, compounds 6-T1 to 6-T15 each comprise SEQ ID NO:6 as the ST receptor binding moiety.

Compounds 7-T1 to 7-T15 are the same as compounds 2-T1 to 2-T15, respectively, except instead of comprising SEQ ID NO:2 as the ST receptor binding moiety, compounds 7-T1 to 7-T15 each comprise SEQ ID NO:7 as the ST receptor binding moiety.

Compounds 8-T1 to 8-T15 are the same as compounds 2-T1 to 2-T15, respectively, except instead of comprising SEQ ID NO:2 as the ST receptor binding moiety, compounds 8-T1 to 8-T15 each comprise SEQ ID NO:8 as the ST receptor binding moiety.

Compounds 9-T1 to 9-T15 are the same as compounds 2-T1 to 2-T15, respectively, except instead of comprising SEQ ID NO:2 as the ST receptor binding moiety, compounds 9-T1 to 9-T15 each comprise SEQ ID NO:9 as the ST receptor binding moiety.

Compounds 10-T1 to 10-T15 are the same as compounds 2-T1 to 2-T15, respectively, except instead of comprising SEQ ID NO:2 as the ST receptor binding moiety, compounds 10-T1 to 10-T15 each comprise SEQ ID NO:2 as the ST receptor binding moiety.

Compounds 11-T1 to 11-T15 are the same as compounds 2-T1 to 2-T15, respectively, except instead of comprising SEQ ID NO:2 as the ST receptor binding moiety, compounds 11-T1 to 11-T15 each comprise SEQ ID NO:11 as the ST receptor binding moiety.

Compounds 12-T1 to 12-T15 are the same as compounds 2-T1 to 2-T15, respectively, except instead of comprising SEQ ID NO:2 as the ST receptor binding moiety, compounds 12-T1 to 12-T15 each comprise SEQ ID NO:12 as the ST receptor binding moiety.

Compounds 13-T1 to 13-T15 are the same as compounds 2-T1 to 2-T15, respectively, except instead of comprising SEQ ID NO:2 as the ST receptor binding moiety, compounds 13-T1 to 13-T15 each comprise SEQ ID NO:13 as the ST receptor binding moiety.

Compounds 14-T1 to 14-T15 are the same as compounds 2-T1 to 2-T15, respectively, except instead of comprising SEQ ID NO:2 as the ST receptor binding moiety, compounds 14-T1 to 14-T15 each comprise SEQ ID NO:14 as the ST receptor binding moiety.

Compounds 15-T1 to 15-T15 are the same as compounds 2-T1 to 2-T15, respectively, except instead of comprising SEQ ID NO:2 as the ST receptor binding moiety, compounds 15-T1 to 15-T15 each comprise SEQ ID NO:15 as the ST receptor binding moiety.

Compounds 15-T1 to 15-T15 are the same as compounds 2-T1 to 2-T15, respectively, except instead of comprising SEQ ID NO:2 as the ST receptor binding moiety, compounds 15-T1 to 15-T15 each comprise SEQ ID NO:15 as the ST receptor binding moiety.

Compounds 17-T1 to 17-T15 are the same as compounds 2-T1 to 2-T15, respectively, except instead of comprising SEQ ID NO:2 as the ST receptor binding moiety, compounds 17-T1 to 17-T15 each comprise SEQ ID NO:17 as the ST receptor binding moiety.

Compounds 18-T1 to 18-T15 are the same as compounds 2-T1 to 2-T15, respectively, except instead of comprising SEQ ID NO:2 as the ST receptor binding moiety, compounds 18-T1 to 18-T15 each comprise SEQ ID NO:18 as the ST receptor binding moiety.

Compounds 19-T1 to 19-T15 are the same as compounds 2-T1 to 2-T15, respectively, except instead of comprising SEQ ID NO:2 as the ST receptor binding moiety, compounds 19-T1 to 19-T15 each comprise SEQ ID NO:19 as the ST receptor binding moiety.

Compounds 20-T1 to 20-T15 are the same as compounds 2-T1 to 2-T15, respectively, except instead of comprising SEQ ID NO:2 as the ST receptor binding moiety, compounds 20-T1 to 20-T15 each comprise SEQ ID NO:20 as the ST receptor binding moiety.

Compounds 21-T1 to 21-T15 are the same as compounds 2-T1 to 2-T15, respectively, except instead of comprising SEQ ID NO:2 as the ST receptor binding moiety, compounds 21-T1 to 21-T15 each comprise SEQ ID NO:21 as the ST receptor binding moiety.

Compounds 22-T1 to 22-T15 are the same as compounds 2-T1 to 2-T15, respectively, except instead of comprising SEQ ID NO:2 as the ST receptor binding moiety, compounds 22-T1 to 22-T15 each comprise SEQ ID NO:22 as the ST receptor binding moiety.

Compounds 23-T1 to 23-T15 are the same as compounds 2-T1 to 2-T15, respectively, except instead of comprising SEQ ID NO:2 as the ST receptor binding moiety, compounds 23-T1 to 23-T15 each comprise SEQ ID NO:23 as the ST receptor binding moiety.

Compounds 24-T1 to 24-T15 are the same as compounds 2-T1 to 2-T15, respectively, except instead of comprising SEQ ID NO:2 as the ST receptor binding moiety, compounds 24-T1 to 24-T15 each comprise SEQ ID NO:24 as the ST receptor binding moiety.

Compounds 25-T1 to 25-T15 are the same as compounds 2-T1 to 2-T15, respectively, except instead of comprising SEQ ID NO:2 as the ST receptor binding moiety, compounds 25-T1 to 25-T15 each comprise SEQ ID NO:25 as the ST receptor binding moiety.

Compounds 26-T1 to 26-T15 are the same as compounds 2-T1 to 2-T15, respectively, except instead of comprising SEQ ID NO:2 as the ST receptor binding moiety, compounds 26-T1 to 26-T15 each comprise SEQ ID NO:26 as the ST receptor binding moiety.

Compounds 27-T1 to 27-T15 are the same as compounds 2-T1 to 2-T15, respectively, except instead of comprising SEQ ID NO:2 as the ST receptor binding moiety, compounds 27-T1 to 27-T15 each comprise SEQ ID NO:27 as the ST receptor binding moiety.

Compounds 28-T1 to 28-T15 are the same as compounds 2-T1 to 2-T15, respectively, except instead of comprising SEQ ID NO:2 as the ST receptor binding moiety, compounds 28-T1 to 28-T15 each comprise SEQ ID NO:28 as the ST receptor binding moiety.

Compounds 29-T1 to 29-T15 are the same as compounds 2-T1 to 2-T15, respectively, except instead of comprising SEQ ID NO:2 as the ST receptor binding moiety, compounds 29-T1 to 29-T15 each comprise SEQ ID NO:29 as the ST receptor binding moiety.

Compounds 30-T1 to 30-T15 are the same as compounds 2-T1 to 2-T15, respectively, except instead of comprising SEQ ID NO:2 as the ST receptor binding moiety, compounds 30-T1 to 30-T15 each comprise SEQ ID NO:30 as the ST receptor binding moiety.

Compounds 31-TI to 31-T15 are the same as compounds 2-T1 to 2-T15, respectively, except instead of comprising SEQ ID NO:2 as the ST receptor binding moiety, compounds 31-T1 to 31-TIS each comprise SEQ ID NO:31 as the ST receptor binding moiety.

Compounds 32-T1 to 32-T15 are the same as compounds 2-T1 to 2-T15, respectively, except instead of comprising SEQ ID NO:2 as the ST receptor binding moiety, compounds 32-T1 to 32-T15 each comprise SEQ ID NO:32 as the ST receptor binding moiety.

Compounds 33-T1 to 33-T15 are the same as compounds 2-T1 to 2-T15, respectively, except instead of comprising SEQ ID NO:2 as the ST receptor binding moiety, compounds 33-T1 to 33-T15 each comprise SEQ ID NO:33 as the ST receptor binding moiety.

Compounds 34-T1 to 34-T15 are the same as compounds 2-T1 to 2-T15, respectively, except instead of comprising SEQ ID NO:2 as the ST receptor binding moiety, compounds 34-T1 to 34-T15 each comprise SEQ ID NO:34 as the ST receptor binding moiety.

Compounds 35-T1 to 35-T15 are the same as compounds 2-T1 to 2-T15, respectively, except instead of comprising SEQ ID NO:2 as the ST receptor binding moiety, compounds 35-T1 to 35-T15 each comprise SEQ ID NO:35 as the ST receptor binding moiety.

Compounds 36-T1 to 36-T15 are the same as compounds 2-T1 to 2-T15, respectively, except instead of comprising SEQ ID NO:2 as the ST receptor binding moiety, compounds 36-T1 to 36-T15 each comprise SEQ ID NO:36 as the ST receptor binding moiety.

Compounds 37-T1 to 37-T15 are the same as compounds 2-T1 to 2-T15, respectively, except instead of comprising SEQ ID NO:2 as the ST receptor binding moiety, compounds 37-T1 to 37-T15 each comprise SEQ ID NO:37 as the ST receptor binding moiety.

Compounds 38-T1 to 38-T15 are the same as compounds 2-T1 to 2-T15, respectively, except instead of comprising SEQ ID NO:2 as the ST receptor binding moiety, compounds 38-T1 to 38-T15 each comprise SEQ ID NO:38 as the ST receptor binding moiety.

Compounds 39-T1 to 39-T15 are the same as compounds 2-T1 to 2-T15, respectively, except instead of comprising SEQ ID NO:2 as the ST receptor binding moiety, compounds 39-T1 to 39-T15 each comprise SEQ ID NO:39 as the ST receptor binding moiety.

Compounds 40-T1 to 40-T15 are the same as compounds 2-T1 to 2-T15, respectively, except instead of comprising SEQ ID NO:2 as the ST receptor binding moiety, compounds 40-T1 to 40-T15 each comprise SEQ ID NO:40 as the ST receptor binding moiety.

Compounds 41-T1 to 41-T15 are the same as compounds 2-T1 to 2-T15, respectively, except instead of comprising SEQ ID NO:2 as the ST receptor binding moiety, compounds 41-T1 to 41-T15 each comprise SEQ ID NO:41 as the ST receptor binding moiety.

Compounds 42-T1 to 42-T15 are the same as compounds 2-T1 to 2-T15, respectively, except instead of comprising SEQ ID NO:2 as the ST receptor binding moiety, compounds 42-T1 to 42-T15 each comprise SEQ ID NO:42 as the ST receptor binding moiety.

Compounds 43-T1 to 43-T15 are the same as compounds 2-T1 to 2-T15, respectively, except instead of comprising SEQ ID NO:2 as the ST receptor binding moiety, compounds 43-T1 to 43-T15 each comprise SEQ ID NO:43 as the ST receptor binding moiety.

Compounds 44-T1 to 44-T15 are the same as compounds 2-T1 to 2-T15, respectively, except instead of comprising SEQ ID NO:2 as the ST receptor binding moiety, compounds 44-T1 to 44-T15 each comprise SEQ ID NO:44 as the ST receptor binding moiety.

Compounds 45-T1 to 45-T15 are the same as compounds 2-T1 to 2-T15, respectively, except instead of comprising SEQ ID NO:2 as the ST receptor binding moiety, compounds 45-T1 to 45-T15 each comprise SEQ ID NO:45 as the ST receptor binding moiety.

Compounds 46-T1 to 46-T15 are the same as compounds 2-T1 to 2-T15, respectively, except instead of comprising SEQ ID NO:2 as the ST receptor binding moiety, compounds 46-T1 to 46-T15 each comprise SEQ ID NO:46 as the ST receptor binding moiety.

Compounds 47-T1 to 47-T15 are the same as compounds 2-T1 to 2-T15, respectively, except instead of comprising SEQ ID NO:2 as the ST receptor binding moiety, compounds 47-T1 to 47-T15 each comprise SEQ ID NO:47 as the ST receptor binding moiety.

Compounds 48-T1 to 48-T15 are the same as compounds 2-T1 to 2-T15, respectively, except instead of comprising SEQ ID NO:2 as the ST receptor binding moiety, compounds 48-T1 to 48-T15 each comprise SEQ ID NO:48 as the ST receptor binding moiety.

Compounds 49-T1 to 49-T15 are the same as compounds 2-T1 to 2-T15, respectively, except instead of comprising SEQ ID NO:2 as the ST receptor binding moiety, compounds 49-T1 to 49-T15 each comprise SEQ ID NO:49 as the ST receptor binding moiety.

Compounds 50-T1 to 50-T15 are the same as compounds 2-T1 to 2-T15, respectively, except instead of comprising SEQ ID NO:2 as the ST receptor binding moiety, compounds 50-T1 to 50-T15 each comprise SEQ ID NO:50 as the ST receptor binding moiety.

Compounds 51-T1 to 51-T15 are the same as compounds 2-T1 to 2-T15, respectively, except instead of comprising SEQ ID NO:2 as the ST receptor binding moiety, compounds 51-T1 to 51-T15 each comprise SEQ ID NO:51 as the ST receptor binding moiety.

Compounds 52-T1 to 52-T15 are the same as compounds 2-T1 to 2-T15, respectively, except instead of comprising SEQ ID NO:2 as the ST receptor binding moiety, compounds 52-T1 to 52-T15 each comprise SEQ ID NO:52 as the ST receptor binding moiety.

Compounds 53-T1 to 53-T15 are the same as compounds 2-T1 to 2-T15, respectively, except instead of comprising SEQ ID NO:2 as the ST receptor binding moiety, compounds 53-T1 to 53-T15 each comprise SEQ ID NO:53 as the ST receptor binding moiety.

Compounds 54-T1 to 54-T15 are the same as compounds 2-T1 to 2-T15, respectively, except instead of comprising SEQ ID NO:2 as the ST receptor binding moiety, compounds 54-T1 to 54-T15 each comprise SEQ ID NO:54 as the ST receptor binding moiety.

Compounds 2-AP, 3-AP and 5-AP to 54-AP refer to the 51 conjugated compounds that comprise alkaline phosphatase conjugated to SEQ ID NO:2, SEQ ID NO:3 and SEQ ID NO:5 through SEQ ID NO:54, respectively.

Compounds 2-NIZ, 3-NIZ and 5-NIZ to 54-NIZ refer to the 51 conjugated compounds that comprise nitroimidazole conjugated to SEQ ID NO:2, SEQ ID NO:3 and SEQ ID NO:5 through SEQ ID NO:54, respectively.

Compounds 2-MEZ, 3-MEZ and 5-MEZ to 54-MEZ refer to the 51 conjugated compounds that comprise metronidazole conjugated to SEQ ID NO:2, SEQ ID NO:3 and SEQ ID NO:5 through SEQ ID NO:54, respectively.

Compounds 2-MIS, 3-MIS and 5-MIS to 54-MIS refer to the 51 conjugated compounds that comprise misonidazole conjugated to SEQ ID NO:2, SEQ ID NO:3 and SEQ ID NO:5 through SEQ ID NO:54, respectively.

Compounds 2-47Sc, 3-47Sc and 5-47Sc to 54-47Sc refer to the 51 conjugated compounds that comprise $^{47}$Sc conjugated to SEQ ID NO:2, SEQ ID NO:3 AND SEQ ID NO:5 through SEQ ID NO:54, respectively.

Compounds 2-67Cu, 3-67Cu and 5-67Cu to 54-67Cu refer to the 51 conjugated compounds that comprise $^{67}$Cu conjugated to SEQ ID NO:2, SEQ ID NO:3 AND SEQ ID NO:5 through SEQ ID NO:54, respectively.

Compounds 2-90Y, 3-90Y and 5-90Y to 54-90Y refer to the 51 conjugated compounds that comprise $^{90}$Y conjugated to SEQ ID NO:2, SEQ ID NO:3 AND SEQ ID NO:5 through SEQ ID NO:54, respectively.

Compounds 2-109Pd, 3-109Pd and 5-109Pd to 54-109Pd refer to the 51 conjugated compounds that comprise $^{109}$Pd conjugated to SEQ ID NO:2, SEQ ID NO:3 AND SEQ ID NO:5 through SEQ ID NO:54, respectively.

Compounds 2-123I, 3-123I and 5-123I to 54-123I refer to the 51 conjugated compounds that comprise $^{123}$I conjugated to SEQ ID NO:2, SEQ ID NO:3 AND SEQ ID NO:5 through SEQ ID NO:54, respectively.

Compounds 2-125I, 3-125I and 5-125I to 54-125I refer to the 51 conjugated compounds that comprise $^{125}$I conjugated to SEQ ID NO:2, SEQ ID NO:3 AND SEQ ID NO:5 through SEQ ID NO:54, respectively.

Compounds 2-131I, 3-131I and 5-131I to 54-131I refer to the 51 conjugated compounds that comprise $^{131}$I conjugated to SEQ ID NO:2, SEQ ID NO:3 AND SEQ ID NO:5 through SEQ ID NO:54, respectively.

Compounds 2-132I, 3-132I and 5-132I to 54-132I refer to the 51 conjugated compounds that comprise $^{132}$I conjugated to SEQ ID NO:2, SEQ ID NO:3 AND SEQ ID NO:5 through SEQ ID NO:54, respectively.

Compounds 2-186Re, 3-186Re and 5-186Re to 54-186Re refer to the 51 conjugated compounds that comprise $^{186}$Re, conjugated to SEQ ID NO:2, SEQ ID NO:3 AND SEQ ID NO:5 through SEQ ID NO:54, respectively.

Compounds 2-188Re, 3-188Re and 5-188Re to 54-188Re refer to the 51 conjugated compounds that comprise $^{188}$Re, conjugated to SEQ ID NO:2, SEQ ID NO:3 AND SEQ ID NO:5 through SEQ ID NO:54, respectively.

Compounds 2-199Au, 3-199Au and 5-199Au to 54-199Au refer to the 51 conjugated compounds that comprise $^{199}$Au, conjugated to SEQ ID NO:2, SEQ ID NO:3 AND SEQ ID NO:5 through SEQ ID NO:54, respectively.

Compounds 2-211At, 3-211At and 5-211At to 54-211At refer to the 51 conjugated compounds that comprise $^{211}$At, conjugated to SEQ ID NO:2, SEQ ID NO:3 AND SEQ ID NO:5 through SEQ ID NO:54, respectively.

Compounds 2-212Pb, 3-212Pb and 5-212Pb to 54-212Pb refer to the 51 conjugated compounds that comprise $^{212}$Pb conjugated to SEQ ID NO:2, SEQ ID NO:3 AND SEQ ID NO:5 through SEQ ID NO:54, respectively.

Compounds 2-212Bi, 3-212Bi and 5-212Bi to 54-212Bi refer to the 51 conjugated compounds that comprise $^{212}$Bi conjugated to SEQ ID NO:2, SEQ ID NO:3 AND SEQ ID NO:5 through SEQ ID NO:54, respectively.

Compounds 2-203Pb, 3-203Pb and 5-203Pb to 54-203Pb refer to the 51 conjugated compounds that comprise $^{203}$Pb conjugated to SEQ ID NO:2, SEQ ID NO:3 AND SEQ ID NO:5 through SEQ ID NO:54, respectively.

Compounds 2-206Bi, 3-206Bi and 5-206Bi to 54-206Bi refer to the 51 conjugated compounds that comprise $^{206}$Bi conjugated to SEQ ID NO:2, SEQ ID NO:3 AND SEQ ID NO:5 through SEQ ID NO:54, respectively.

Compounds 2-32P, 3-32P and 5-32P to 54-32P refer to the 51 conjugated compounds that comprise $^{32}$P conjugated to SEQ ID NO:2, SEQ ID NO:3 AND SEQ ID NO:5 through SEQ ID NO:54, respectively.

Compounds 2-33P, 3-33P and 5-33P to 54-33P refer to the 51 conjugated compounds that comprise $^{33}$P conjugated to SEQ ID NO:2, SEQ ID NO:3 AND SEQ ID NO:5 through SEQ ID NO:54, respectively.

Compounds 2-71Ge, 3-71Ge and 5-71Ge to 54-71Ge refer to the 51 conjugated compounds that comprise $^{71}$Ge conjugated to SEQ ID NO:2, SEQ ID NO:3 AND SEQ ID NO:5 through SEQ ID NO:54, respectively.

Compounds 2-77As, 3-77As and 5-77As to 54-77As refer to the 51 conjugated compounds that comprise $^{77}$As conjugated to SEQ ID NO:2, SEQ ID NO:3 AND SEQ ID NO:5 through SEQ ID NO:54, respectively.

Compounds 2-103Pd, 3-103Pd and 5-103Pd to 54-103Pd refer to the 51 conjugated compounds that comprise $^{103}$Pd conjugated to SEQ ID NO:2, SEQ ID NO:3 AND SEQ ID NO:5 through SEQ ID NO:54, respectively.

Compounds 2-105Rh, 3-105Rh and 5-105Rh to 54-105Rh refer to the 51 conjugated compounds that comprise $^{105}$Rh conjugated to SEQ ID NO:2, SEQ ID NO:3 AND SEQ ID NO:5 through SEQ ID NO:54, respectively.

Compounds 2-111Ag, 3-111Ag and 5-111Ag to 54-111Ag refer to the 51 conjugated compounds that comprise $^{111}$Ag conjugated to SEQ ID NO:2, SEQ ID NO:3 AND SEQ ID NO:5 through SEQ ID NO:54, respectively.

Compounds 2-119Sb, 3-119Sb and 5-119Sb to 54-119Sb refer to the 51 conjugated compounds that comprise $^{119}$Sb conjugated to SEQ ID NO:2, SEQ ID NO:3 AND SEQ ID NO:5 through SEQ ID NO:54, respectively.

Compounds 2-121Sn, 3-121-Sn and 5-121Sn to 54-121Sn refer to the 51 conjugated compounds that comprise $^{121}$Sn conjugated to SEQ ID NO:2, SEQ ID NO:3 AND SEQ ID NO:5 through SEQ ID NO:54, respectively.

Compounds 2-131Cs, 3-131Cs and 5-131Cs to 54-131Cs refer to the 51 conjugated compounds that comprise $^{131}$Cs conjugated to SEQ ID NO:2, SEQ ID NO:3 AND SEQ ID NO:5 through SEQ ID NO:54, respectively.

Compounds 2-127Cs, 3-131Cs and 5-131Cs to 54-127Cs refer to the 51 conjugated compounds that comprise $^{127}$Cs conjugated to SEQ ID NO:2, SEQ ID NO:3 AND SEQ ID NO:5 through SEQ ID NO:54, respectively.

Compounds 2-129Cs, 3-129Cs and 5-129Cs to 54-129Cs refer to the 51 conjugated compounds that comprise $^{129}$Cs conjugated to SEQ ID NO:2, SEQ ID NO:3 AND SEQ ID NO:5 through SEQ ID NO:54, respectively.

Compounds 2-143Pr, 3-143Pr and 5-143Pr to 54-143Pr refer to the 51 conjugated compounds that comprise $^{143}$Pr conjugated to SEQ ID NO:2, SEQ ID NO:3 AND SEQ ID NO:5 through SEQ ID NO:54, respectively.

Compounds 2-161Tb, 3-161Tb and 5-161Tb to 54-161Tb refer to the 51 conjugated compounds that comprise $^{161}$Tb conjugated to SEQ ID NO:2, SEQ ID NO:3 AND SEQ ID NO:5 through SEQ ID NO:54, respectively.

Compounds 2-177Lu, 3-177Lu and 5-177Lu to 54-177Lu refer to the 51 conjugated compounds that comprise $^{177}$Lu conjugated to SEQ ID NO:2, SEQ ID NO:3 AND SEQ ID NO:5 through SEQ ID NO:54, respectively.

Compounds 2-191Os, 3-191Os and 5-191Os to 54-191Os refer to the 51 conjugated compounds that comprise 191Os conjugated to SEQ ID NO:2, SEQ ID NO:3 AND SEQ ID NO:5 through SEQ ID NO:54, respectively.

Compounds 2-193mPt, 3-193mPt and 5-193mPt to 54-193mPt refer to the 51 conjugated compounds that comprise $^{193M}$Pt conjugated to SEQ ID NO:2, SEQ ID NO:3 AND SEQ ID NO:5 through SEQ ID NO:54, respectively.

Compounds 2-197Hg, 3-197Hg and 5-197Hg to 54-197Hg refer to the 51 conjugated compounds that comprise $^{197}$Hg conjugated to SEQ ID NO:2, SEQ ID NO:3 AND SEQ ID NO:5 through SEQ ID NO:54, respectively.

Compounds 2-43K, 3-43K and 5-43K to 54-43K refer to the 51 conjugated compounds that comprise $^{43}$K conjugated to SEQ ID NO:2, SEQ ID NO:3 AND SEQ ID NO:5 through SEQ ID NO:54, respectively.

Compounds 2-52Fe, 3-52Fe and 5-52Fe to 54-52Fe refer to the 51 conjugated compounds that comprise $^{52}$Fe conjugated to SEQ ID NO:2, SEQ ID NO:3 AND SEQ ID NO:5 through SEQ ID NO:54, respectively.

Compounds 2-57Co, 3-57Co and 5-57Co to 54-57Co refer to the 51 conjugated compounds that comprise $^{57}$Co conjugated to SEQ ID NO:2, SEQ ID NO:3 AND SEQ ID NO:5 through SEQ ID NO:54, respectively.

Compounds 2-67Ga, 3-67Ga and 5-67Ga to 54-67Ga refer to the 51 conjugated compounds that comprise $^{67}$Ga conjugated to SEQ ID NO:2, SEQ ID NO:3 AND SEQ ID NO:5 through SEQ ID NO:54, respectively.

Compounds 2-68Ga, 3-68Ga and 5-68Ga to 54-68Ga refer to the 51 conjugated compounds that comprise $^{68}$Ga conjugated to SEQ ID NO:2, SEQ ID NO:3 AND SEQ ID NO:5 through SEQ ID NO:54, respectively.

Compounds 2-77Br, 3-77Br and 5-77Br to 54-77Br refer to the 51 conjugated compounds that comprise $^{77}$Br conjugated to SEQ ID NO:2, SEQ ID NO:3 AND SEQ ID NO:5 through SEQ ID NO:54, respectively.

Compounds 2-81Rb, 3-81Rb and 5-81Rb to 54-81Rb refer to the 51 conjugated compounds that comprise $^{81}$Rb conjugated to SEQ ID NO:2, SEQ ID NO:3 AND SEQ ID NO:5 through SEQ ID NO:54, respectively.

Compounds 2-81mKr, 3-81mKr and 5-81mKr to 54-81mKr refer to the 51 conjugated compounds that comprise $^{81M}$Kr conjugated to SEQ ID NO:2, SEQ ID NO:3 AND SEQ ID NO:5 through SEQ ID NO:54, respectively.

Compounds 2-87mSr, 3-87mSr and 5-87mSr to 54-87mSr refer to the 51 conjugated compounds that comprise $^{87M}$Sr conjugated to SEQ ID NO:2, SEQ ID NO:3 AND SEQ ID NO:5 through SEQ ID NO:54, respectively.

Compounds 2-99mTc, 3-99mTc and 5-99mTc to 54-99mTc refer to the 51 conjugated compounds that comprise $^{99M}$Tc conjugated to SEQ ID NO:2, SEQ ID NO:3 AND SEQ ID NO:5 through SEQ ID NO:54, respectively.

Compounds 2-111In, 3-111In and 5-111In to 54-111In refer to the 51 conjugated compounds that comprise $^{111}$In conjugated to SEQ ID NO:2, SEQ ID NO:3 AND SEQ ID NO:5 through SEQ ID NO:54, respectively.

Compounds 2-113mIn, 3-113mIn and 5-113mIn to 54-113mIn refer to the 51 conjugated compounds that comprise $^{113M}$In conjugated to SEQ ID NO:2, SEQ ID NO:3 AND SEQ ID NO:5 through SEQ ID NO:54, respectively.

The compounds described in this example are combined with a pharmaceutically acceptable carrier or diluent to produce pharmaceutical compositions according to the present invention. Radiostable compounds described herein are useful in pharmaceutical compositions as therapeutics in the treatment of individuals suspected of suffering from metastasized colorectal cancer including treatment of individuals diagnosed with localized colorectal cancer as a prophylactic/therapeutic before metastasis can be readily detected. When present in therapeutically effective amounts, radioactive compounds described herein are useful in pharmaceutical compositions as therapeutic agents in the treatment of individuals suspected of suffering from metastasized colorectal cancer including treatment of individuals diagnosed with localized colorectal cancer as a prophylactic/therapeutic before metastasis can be readily detected. When present in diagnostically effective amounts, radioactive compounds described herein are useful in pharmaceutical compositions as imaging agents in the diagnosis and identification of metastasized colorectal cancer in individuals.

Example 2

One procedure for crosslinking ST receptor ligands which have a free amino group such as ST receptor binding peptides, as for example SEQ ID NO:2, SEQ ID NO:3, and SEQ ID NOS:5-54 to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with chain carbon spacers such as disuccinimidyl suberate (Pierce Co, Rockford, Ill.). This approach of amino group derivatization has been employed successfully to crosslink native ST to biotin and, ultimately, to large agarose beads of micron-scale size, preserving the function of native ST (Hughes, M., et al. (1991) *Biochem.* 30:10738; Hakki, S., et al. (1993) *Int. J. Biochem.* 25:557; Almenoff, J. S., et al. (1992) *Mol. Micro.* 8:865; each of which is incorporated herein by reference).

An ST binding ligand with the free amino group such as an ST receptor binding peptide is incubated in the presence of the chemical crosslinking agent and an active agent which have a free amino group in equimolar quantities at room temperature for 15–30 min. Incubation is terminated by separating the reactants by gel permeation chromatography by HPLC. This technique separates the conjugated compounds from free active agents and free ST binding ligands, active agent-active agent conjugates and ST binding ligand-ST binding ligand conjugates. Homogeneous preparations of conjugated through their free amino groups and with a preferred molar ratio of 1:1 are obtained. As indicated above, complexing the free amino group of an ST peptide preserves receptor binding function.

Example 3

In the event that a cleavable conjugated compound is required, the same protocol as described above may be employed utilizing 3,3'-dithiobis (sulfosuccinimidylpropionate (SPDP) Pierce, Ill.). SPDP forms a sulfhydryl group from a free amino group which may be used to conjugate a compound to another free amino group. For example, ST peptides such as SEQ ID NO:2, SEQ ID NO:3, SEQ ID NOS:5–54 are derivatized using established procedures employing N-succinimidyl-3 (2-pyridildithio)-propionate (SPDP, Pharmacia-LKB, NJ). The ST peptide is incubated with a 5-fold molar excess of SPDP for 30 minutes at room temperature. The ST-pyridylthiopropionate conjugate is separated from unreacted reagents by gel permeation chromatography by HPLC. An active agent with a free amino group, such as a protein-based toxin, is prepared for conjugation by reduction with dithiothreitol for 4 hours at room temperature. Reduced active agent is incubated with a 2-fold molar excess of ST receptor ligand-PDP conjugate at pH 8.0 for 36 hours at 4©C. Conjugate compound is purified from unreacted agents by gel permeation chromatography by HPLC.

This protocol for conjugation is particularly useful to conjugate ST peptides to diphtheria toxin A chains and Pseudomonas exotoxin as well as ricin toxin A chains (Magerstadt, M. *Antibody Conjugates and Malignant Disease.* (1991) CRC Press, Boca Raton, USA, pp. 110–152; Cawley, D. B. et al. (1980) *Cell* 22:563; Cumber, A. J., et al. (1985) *Meth. Enz.* 112:207; Gros, O. (1985) *J. Immunol. Meth.* 81:283; Worrell, N. R., et al. (1986) *Anti-Cancer Drug Design* 1:179; Thorpe, P. E. et al. (1987) *Cancer Res.* 47:5924, each of which is incorporated herein by reference).

Example 4

Active agents with a free amino group may be derivatized with SPDP as described above and conjugated with an ST ligand that has a free amino group and that has been modified with the succinimidyl ester of iodoacetic acid (Pierce Co., Rockford, Ill.) (Magerstadt, M. (1991) *Antibody*

*Conjugates And Malignant Disease*, CRC Press Boca Raton; Cumber, A. J. et al. (1985) *Meth. Enz.* 112:20, which are incorporated herein by reference). Conjugation relies on the selective reaction of iodoacetyl groups introduced into the amino terminal of the ST ligand with the thiol groups introduced into the active agent. As with the above protocol, this procedure avoids homopolymer formation. However, the product is conjugated through a central thioether linkage which cannot be reduced.

Example 5

An ST receptor ligand with a free amino group and active agents with free amino groups may be conjugated through a disulfide bond using iminothiolane (Pierce, Rockford, Ill.) (Fitzgerald, D. J. P. et al. (1983) *Cell* 32:607; Magerstadt, M. (1991) *Antibody Conjugates And Malignant Disease*, CRC Press, Boca Raton; Bjorn, M. J., et al. (1985) *Cancer Res.* 45:1214; Bjorn, M. J., et al. (1986) *Cancer Res.* 46:3262, which are incorporated herein by reference). The ST receptor ligand with a free amino group is derivatized at the amino terminal with iminothiolane and the active agent is derivatized with SPDP as described above. Reacting iminothiolane-derivatized ST receptor ligand with SPDP-derivatized active agent results in conjugation by a reducible disulfide bond. In addition, iminothiolane provides the versatility to conjugate these proteins through bonds other than disulfides. Thus, derivatization of active agents with the heterobifunctional agent sulfosuccinimidyl 4-(N-maleimidomethyl) cyclohexane (Pierce, Rockford, Ill.) and reaction with iminothiolane-derivatized ST receptor ligand will conjugate these peptides without formation of disulfides.

Example 6

Conjugated compounds according to the invention which comprise an active moiety that is a therapeutic agent specifically inhibit T84 cells in vitro. The following protocols may be used to demonstrate that the conjugated compounds according to the invention which comprise an active moiety that is chemotherapeutic or toxin specifically inhibit T84 cells in vitro. Inhibition of T84 cells is assessed by determining the effects of conjugated compounds on the ability of T84 cells to incorporate $^{35}$S-leucine into protein, $^{3}$H-thymidine into DNA, and to form colonies. The assessment of protein and DNA synthesis are classical techniques to determine the cytotoxicity of conjugated compounds in vitro. Inhibition of protein synthesis is measured because the toxins used as active moieties are specific inhibitors of this process. Therefore, these assays are the most sensitive measure of whether conjugated compounds are binding to and internalized into T84 cells. Inhibition of DNA synthesis is measured because some chemotherapeutics inhibit DNA synthesis and further, it is a cytotoxicity assay which correlates closely with the reproductive survivability of cells in culture. Cytotoxicity, or the disruption of normal cellular metabolic processes, may not always directly correlate with cell survivability. Therefore, assessment of colony formation will directly measure the ability of the experimental agents to decrease the survivability of tumor cells, which closely correlates with the impact of therapeutic agents on tumor viability in vivo. Controls include performing the same assay using the unconjugated form of the active agent and the unconjugated form of the ST receptor ligand of which the conjugated compound is comprised in place of the conjugated compound. The results obtained in the test assays and control assays are compared.

Conjugated compounds are assessed for their ability to inhibit protein and DNA synthesis in vitro and to inhibit survival and proliferation by measuring colony formation in monolayer culture by established protocols (Wilson, A. P. (1987) "Cytotoxicity and viability assays", Animal Cell Culture: A Practical Approach. Freshney, R. I., ed. pp. 183–216, IRL Press, Oxford. which is incorporated herein by reference).

To assess the ability of a conjugated compound to inhibit protein synthesis in vitro, cells are plated in 200 $\mu$l of medium at a sub-confluent density of 1–2×$10^5$ and allowed to attach to form a dividing cell monolayer over 12 hours at 37° C. Subsequently, the media is replaced with 200 $\mu$l of fresh media containing the appropriate concentration of conjugated compounds and cells incubated at 37° C. for various amounts of time. At the end of the indicated incubation period, cells is washed twice with medium and incubated at 37° C. in 0.5 ml of methionine-free medium supplemented with 0.5 $\mu$Ci of L$^{35}$S-methionine (800 Ci/mmol). After incubation for another 2 hours at 37° C., the medium is aspirated, cells washed twice with medium containing 1 mg/ml of methionine, and then precipitated in 12% ice-cold TCA. Radioactivity recovered in TCA precipitates by centrifugation is quantified by liquid scintillation spectroscopy. In these studies, cells are maintained in log growth and assays are performed using triplicate wells. Data is expressed as a percentage of protein synthesis observed in the presence of experimental agents compared to untreated cells.

To assess the ability of a conjugated compound to inhibit DNA synthesis in vitro cells are plated as a subconfluent monolayer and incubated with experimental agents as described above. At the end of the incubation period, cells are washed twice and incubated at 37° C. in medium containing 2.5 $\mu$Ci of $^{3}$H-thymidine (5 Ci/mmol). After incubation for another hour, cells are processed with TCA, precipitates recovered, and radioactivity quantified as described above. As above, cells are maintained in log growth and assays is performed in triplicate. Data is expressed as a percentage of DNA synthesis observed in the presence of experimental agents compared to untreated cells.

To assess the ability of a conjugated compound to inhibit survival and proliferation by measuring colony formation in monolayer culture, cells are plated as a sub-confluent monolayer on 25 cm$^2$ flasks and allowed to attach as described above. The medium is replaced with that containing various concentrations of experimental agents and incubated with cells for various amounts of time. At the end of the incubation, cells are recovered as a single cell suspension by trypsinization and replated to a density which will yield 100–200 colonies per 6 cm plate. Cells are permitted to grow for 7 days, then fixed in methanol, stained with 1% crystal violet, and the number of colonies quantified. Assays are performed in duplicate and data is expressed as a percentage of colony formation observed in the presence of experimental agents compared to untreated cells. Results in our laboratory have demonstrated that T84 cells can be placed into single cell suspensions utilizing trypsin (10 $\mu$g/ml) with a plating efficiency of 40% and a doubling time of 18 hours.

Example 7

Radioactive iodine such as $^{123}$I, $^{125}$I, $^{131}$I and $^{132}$I, can be added to an ST receptor binding peptide such as an ST peptide using a standard protocol well-known to those having ordinary skill in the art (Thompson, M. et al. (1985)

Analytical Biochemistry 148:26, which is incorporated herein by reference). Radioactive iodine is conjugated directly to an ST peptide such as SEQ ID NO:2, SEQ ID NO:3 or SEQ ID NO:5 at tyrosine-5, tyrosine-4 or tyrosine-5, respectively.

Briefly, the ST peptide is produced in bacteria. For example, *E. coli* strain 431 is grown in culture and secretes ST into this culture. The culture media is then purified using routine techniques. ST can also be made by solid-phase synthesis as has been done previously, using standard techniques. (Dreyfus, L., et al. (1983) *Infec. Immun.* 42:539, which is incorporated herein by reference.

Ten micrograms of ST peptide are reacted with 2 milli-Curies of radioactive INa (Amersham Corporation, Massachusetts) in the presence of Iodobeads (Bio Rad Laboratories, CA) and beta-D-glucose. These are reacted for 30 min after which the products are subjected to chromatography on a Sepak reversed-phase cartridge (Millipore Corp., MA) followed by separation on a $C_{18}$reversed-phase column by HPLC using a 20–25% acetonitrile gradient. Conjugated compositions which comprise SEQ ID NO:2, SEQ ID NO:3 or SEQ ID NO:5 with the radioiodine attached to tyrosine-4 elutes at 45 min. These molecules retain full biochemical and pharmacological activity.

Example 8

$^{125}$I is conjugated directly to an ST peptide such as SEQ ID NO:13 at tyrosine-4.

SEQ ID NO:13 is produced by solid-phase synthesis as described above. Ten micrograms of SEQ ID NO:13 are reacted with 2 milliCuries of $^{125}$INa (Amersham Corporation, Massachusetts) in the presence of Iodobeads (Bio Rad Laboratories, CA) and beta-D-glucose. These are reacted for 30 min after which the products are subjected to chromatography on a Sepak reversed-phase cartridge (Millipore Corp., MA) followed by separation on a $C_{18}$reversed-phase column by HPLC using a 20–25% acetonitrile gradient. $^{125}$I-SEQ ID NO:13 conjugate with the radioiodine attached to tyrosine-4 elutes at 45 min. This molecule retains full biochemical and pharmacological activity.

Dosing of radioiodine for diagnostic imaging typically requires about 4 milliCuries/patient (Steinstraber, A., et al. (1988) *J. Nucl. Med.* 29:875; Wessels, B. W. and Rogus, R. D. (1984) *Med. Phys.* 11:638; Kwok, C. S., et al. (1985) *Med. Phys.* 12:405). For proteins labelled with a specific activity of 2,000 Curies/mmol, such as ST peptide, this would require about 10 micrograms of labelled peptide injected intravenously .per patient for diagnostic imaging.

Example 9

$^{131}$I is conjugated directly to an ST peptide such as SEQ ID NO:13 at tyrosine-4.

SEQ ID NO:13 is produced by solid-phase synthesis as described above. Ten micrograms of SEQ ID NO:13 are reacted with 10 milliCuries of $^{131}$INa (Amersham Corporation, Massachusetts) in the presence of Iodobeads (Bio Rad Laboratories, CA) and beta-D-glucose. These are reacted for 30 min after which the products are subjected to chromatography on a Sepak reversed-phase cartridge (Millipore Corp., MA) followed by separation on a $C_{18}$reversed-phase column by HPLC using a 20–25% acetonitrile gradient. $^{131}$I-SEQ ID NO:13 conjugate with the radioiodine attached to tyrosine-4 elutes at 45 min. This molecule retains full biochemical and pharmacological activity.

Typically, for radioiodinated antibodies (MW=160,000 Da), about 150 nanomoles of protein (24 milligrams) labelled with a specific activity of 10,000 Curies/mmol are required per gram of tumor per patient (Humm, J. L. (1986) *J. Nucl. Med.* 27:1490). Thus, for proteins labelled with a specific activity of 2,000 Curies/mmol, with a molecular weight of 2,000 Da, such as ST peptide, about 3 milligrams would be required per gram of tumor per patient for intravenous infusion.

Example 10

In some embodiments, coupling of ST receptor ligands which have a free amino group, particularly ST receptor binding peptides such as ST peptides, and active agents with a free amino group such as protein-based toxins is performed by introducing a disulfide bridge between the 2 molecules. This strategy is particularly useful to conjugate ST peptides since the free amino terminal has been shown to be useful as a point of conjugation without affecting ST binding activity. This strategy is particularly useful to conjugate protein-based toxins since the free amino terminal is available on such molecules and for some conjugated compounds, most notably RTA conjugates, a disulfide bride which can be reduced to yield separate proteins has been demonstrated to be important in the construction of functional chimeras targeted by monoclonal antibodies (Magerstadt, M. (1991) *Antibody Conjugates And Malignant Disease*, CRC Press, Boca Raton; Bjorn, M. J., et al. (1985) *Cancer Res.* 45:1214; Bjorn, M. J., et al. (1986) *Cancer Res.* 46:3262; Masuho, Y., et al. (1982) *J. Biochem.* 91:1583, which are each incorporated herein by reference). While some toxins may be coupled to ST peptides using crosslinking agents which do not result in a reducible disulfide bridge between the individual components but retain functional cytotoxicity, ricin A chain toxin requires a reducible disulfide for cytotoxicity while Pseudomonas exotoxin, for example, does not.

Disulfide coupling is achieved using established procedures employing the heterobifunctional agent N-succinimidyl-3 (2-pyridyldithio)-proportionate (SPDP, Pharmacia-LKB, Piscataway, N.J.) (Magerstadt, M. (1991) *Antibody Conjugates And Malignant Disease*, CRC Press, Boca Raton; Cawley, D. B. et al. (1980) *Cell* 22:563; Cumber, A. J., et al. (1985) *Meth. Enz.* 112:20; Gros, O., et al. (1985) *J. Immunol. Meth.* 81:283; Worrell, N. R., (1986) *Anti-Cancer Drug Design* 1:19; Thorpe, P. E., et al. (1987) *Cancer Res.* 4:5924, which are incorporated herein by reference).

In some embodiments, toxins including the A chains of deglycosylated ricin toxin (RTA; Sigma Chemical Co., St. Louis, Mo.), diphtheria toxin A (DTA; Calbiochem, La Jolla, Calif.) and Pseudomonas exotoxin (PEA) are conjugated to ST peptides to produce conjugated compositions according to the present invention using this procedure. Deglycosylated RTA is employed since the glycosylated form of this toxin exhibits non-specific binding to liver cells. DTA is prepared from diphtheria toxin by an established procedure (Michel, A. and Drykx, J. (1975) *Biochem. Biophys. Acta* 365:15; Cumber, A. J., et al. (1985) *Meth. Enz.* 112:207, both of which are incorporated herein by reference). PEA In some embodiments, ST peptides are conjugated to toxins by this procedure. For example, the ST peptide SEQ ID NO:3 which is produced as described above (see Dreyfus, L., et al. (1983) *Infec. Immun.* 42:539, which is incorporated herein by reference).

Toxins are prepared for coupling by reduction with 0.1 M dithiothreitol (DTT) for 4 hours at room temperature in 0.4

M Tris-HCl, pH 8.0 and 1 mM EDTA. Reduced toxins are desalted on a Sephadex G-25 column equilibrated in TES buffer and mixed with a 2-fold molar excess of ST-PDP. Reactions are adjusted to pH 8.0 with TES and incubated at 4° C. for 36 hours. ST peptide-toxin conjugates are purified from unreacted products and homopolymers of ST peptides and toxins by gel filtration on Sephadex G-75 in 20 mM TES, pH 8.0 containing 0.1 M NaCl. Chromatographic fractions are monitored by SDS-PAGE on 10% polyacrylamide gels under non-reducing conditions for the presence of 1:1 conjugates of ST peptides and toxins. Also, these conjugates are analyzed by 10% SDS-PAGE under reducing conditions, to insure that ST and cytotoxins are coupled by a reducible disulfide bond. Molar concentrations of the conjugate are calculated by quantifying radioactivity in these samples.

ST trace labelled with $^{125}$I on tyrosine 4 (10 Ci/mmol) is used in order to follow the conjugate through various separation and chromatographic steps and to enable us to calculate the molar ratio of ST to cytotoxin in the final purified conjugate. ST trace labelled with $^{125}$I is derivatized by incubating 1 mg/ml with a 5-fold molar excess of SPDP for 30 min at room temperature in Na phosphate buffer, pH 7.4. The ST-pyridylthiopropionate (ST-PDP) conjugate is purified from unreacted crosslinking agent by chromatography on Sephadex G-25 equilibrated with 20 mM N-Tris (hydroxymethyl)-methyl-2-aminoethane sulfonic acid (TES) buffer, pH 7.4. Preservation of receptor binding of conjugated ST peptides in human intestinal membranes is determined in competition assays of increasing concentrations of ST-PDP and $^{125}$I-ST ($5 \times 10^{10}$M), to insure that this process does not destroy the function of the ST receptor ligand.

The above coupling protocol has several advantages for conjugating the various toxins. First, it introduces a reducible disulfide bridge into the conjugated composition, important for RTA cytotoxicity. Also, this technique avoids the exposure of ST peptide to quantitative reduction with DTT which could interrupt its 3 intrachain disulfide bonds important for receptor binding activity. In addition, there is a single group available at the amino terminal of ST peptide for derivatization with SPDP and previous experiments have demonstrated that derivatization of that group preserves the binding properties of the ligand. Therefore, other configurations for conjugation which could result in inactivation of ST are not possible. Furthermore, PEA requires preactivation with DTT to achieve optimum cytotoxicity which will be accomplished utilizing the above protocol.

To produce a functional conjugated compound that comprises a toxin, it is essential that the receptor binding and enzyme activities of the moieties are preserved throughout the process of conjugation. Therefore, once such conjugate compounds are obtained, they are tested for the preservation of those functions. ST receptor binding activity of conjugated compounds is examined in competitive binding assays, as described above. In these studies, increasing concentrations of the conjugated compounds are incubated with a constant concentration ($5 \times 10^{10}$M) of $^{125}$I-ST and intestinal membranes (50–100 µg of protein) to achieve equilibrium. Parallel incubations contain excess ($5 \times 10^{7}$M) unlabelled ST to assess non-specific binding. The concentration-dependent competitive displacement of radiolabelled ST by conjugated compounds is compared to the competitive displacement achieved by native ST. Displacement curves are employed to estimate the affinity of each conjugated compound (KD) and compare that to the affinity of native ST measured by this technique. Control studies include evaluating the ability of unconjugated toxins to compete with native ST for receptor binding. These studies establish that the binding function of ST in the conjugated construct is preserved.

Preservation of toxin activity in conjugated compounds is also assessed. PEA and DTA induce toxicity by catalyzing the NAD-dependent ADP-ribosylation of elongation factor 2 (EF2), inhibiting protein synthesis. ADP-ribosyl transferase activity is assessed using an established assay (Chung, D. W. and Collier, R. J. Infect. Immun. 16:832; Fitzgerald, D. J. P. (1987) Meth. Enz. 151:139, which are both incorporated herein by reference). Reactions are conducted in 30 Mm Tris-HCl, pH 8.2 containing 40 mM DTT, 50 mCi $^{14}$C-NAD, and 20 µl of rabbit reticulocyte lysate containing elongation factor 2 (EF-2; Promega, Madison, Wis.) in a total volume of 500 µl. Reactions are initiated by the addition of lysate, incubated for 30 minutes at 37° C., and terminated by the addition of ice-cold 12% TCA. Radioactivity in protein precipitates collected by centrifugation is quantified by liquid scintillation spectroscopy. The ability of the conjugated compounds that comprise DTA or PEA to catalyze the transfer of labelled ADP-ribose to EF-2 is compared to that catalyzed by similar quantities of unconjugated toxins. Control experiments include examining the ability of unconjugated toxins or ST to catalyze ADP-ribose transfer and the effects of ST on the enzymatic activity of unconjugated cytotoxins.

RTA inhibits protein synthesis by catalytically inactivating the 60S ribosomal subunit. The catalytic activity of conjugated compounds that comprise RTA is assessed by its ability to inhibit protein synthesis in cell-free assays using established procedures (Leonard, J. E. et al. (1985) Cancer Res. 45:5263 which is incorporated herein by reference). Assays contain 35 µl of nuclease-treated rabbit reticulocyte lysates, 1 µl of 1 mM mixed amino acids deficient in methionine, 2 µl of Brome mosaic RNA (Promega, Madison, Wis.) at 0.5 µg/µl, 7 µl of sterile water or conjugate solution, and 5 µCi of $^{35}$S-methionine in a total volume of 50 µl. Reactions will be initiated by the addition of lysate, incubated at 30° C. for 30 minutes, and terminated by the use of addition of 12% TCA. Radioactivity in protein precipitates collected by centrifugation is quantified by liquid scintillation spectroscopy. Control experiments include examining the ability of unconjugated RTA or ST peptide to inhibit cell-free protein synthesis and the effects of ST peptide on the inhibitory activity of the unconjugated cytotoxin.

Example 11

Methotrexate is linked to SEQ ID NO:12 by the homobifunctional crosslinker succinimidyl esters with long chain carbon spacers such as disuccinimidyl suberate (Pierce, Ill.). SEQ ID NO:12 is incubated in the presence of the chemical crosslinking agent and methotrexate in equimolar quantities at room temperature for 15–30 min. Incubation is terminated by separating the reactants by gel permeation chromatography by HPLC. This technique separates the methotrexate/SEQ ID NO:12 conjugates from free drug, free ST peptide, drug-drug conjugates and ST peptide-ST peptide conjugates. Homogeneous preparations of SEQ ID NO:12-methotrexate conjugates coupled through their free amino groups and with a preferred molar ratio of 1:1 are obtained. Complexing the free amino group of ST preserves receptor binding function.

Example 12

$^{111}$In is coupled to SEQ ID NO:37 with functional amino groups using a chelator. The ST peptide has a free amino function at the amino terminal which may be modified without altering the ST receptor binding activity of the ST peptide. $^{111}$In is rapidly and potently chelated by either EDTA (ethylenediaminetetraacetic acid) or DTPA (diethylenetriaminepetaacetic acid) . DTPA is preferred over EDTA because the latter may be more unstable in vivo. The $^{111}$In-DTPA is converted to a mixed N-hydroxysuccinimide ester which is reactive with free amino groups, mixed with ST, and the reaction products, including $^{111}$In-SEQ ID NO:37 separated by HPLC (Bremer, K. H. and Schwarz, A. (1987) in *Safety And Efficacy Of Radiopharmaceuticals*. Kristensen, K. and Norbygaard, E., Eds. Martinius Nijhoff, Dordrecht, The Netherlands, P. 43; Krejcarek, G. E., and Tucker, K. L. (1977) *Biochem. Biophys. Res. Commun*. 77:581; Paxton, R. J., et al. (1985) *Cancer Res*. 45:5694; Richardson, A. P., et al. (1986) *Nucl. Med. Biol*. 14:569, which are each incorporated herein by reference).

Example 13

$^{99m}$Tc can be conjugated to SEQ ID NO:46 using an approach which is similar to that for indium. Thus, technetium can be chelated by DTPA which is converted to an anhydride, such as N-hydroxysuccinimide anhydride, and reacted with SEQ ID NO:46. The ST-technetium conjugate can then be separated using HPLC (Magerstadt, M. (1991) *Antibody Conjugates And Malignant Disease* CRC Press, Boca Raton; Eckelman, W. C. and Paik, C. H. (1986) *Nucl. Med. Biol*. 14:569)

Example 14

Diphtheria toxin A chain (DTA) is prepared from native diphtheria toxin by standard techniques. SEQ ID NO:22 is coupled to N-succinimidyl-3 (2-pyridyldithio) -propionate (SPDP, Pharmacia-LKB, Piscataway, N.J.) and the SEQ ID NO:22-PDP conjugate is purified by HPLC by established procedures. DTA is reduced with dithiothreitol and incubated with SEQ ID NO:22-PDP. DTA-SEQ ID NO:22 is purified after conjugation using HPLC.

Example 15

Pseudomonas Exotoxin is prepared from native sources by standard techniques. SEQ ID NO:54 is coupled to N-succinimidyl-3(2-pyridyldithio)-propionate (SPDP, Pharmacia-LKB, Piscataway, N.J.) and the SEQ ID NO:54-PDP conjugate is purified by HPLC by established procedures. Pseudomonas Exotoxin is reduced with dithiothreitol and incubated with SEQ ID NO:54-PDP. Pseudomonas Exotoxin-SEQ ID NO:54 is purified after conjugation using HPLC.

Example 16

Doxorubicin is linked to SEQ ID NO:54 by the homobifunctional crosslinker succinimidyl esters with long chain carbon spacers such as disuccinimidyl suberate (Pierce, Ill.). SEQ ID NO:54 is incubated in the presence of the chemical crosslinking agent and doxorubicin in equimolar quantities at room temperature for 15–30 min. Incubation is terminated by separating the reactants by gel permeation chromatography by HPLC. This technique separates the doxorubicin/SEQ ID NO:54 conjugates from free doxorubicin, free ST peptide, drug-drug conjugates and ST peptide-ST peptide conjugates. Homogeneous preparations of SEQ ID NO:54-doxorubicin conjugates coupled through their free amino groups and with a preferred molar ratio of 1:1 are obtained. Complexing the free amino group of ST preserves receptor binding function.

Example 17

Daunorubicin is linked to SEQ ID NO:32 by the homobifunctional crosslinker succinimidyl esters with long chain carbon spacers such as disuccinimidyl suberate (Pierce, Ill.). SEQ ID NO:32 is incubated in the presence of the chemical crosslinking agent and daunorubicin in equimolar quantities at room temperature for 15–30 min. Incubation is terminated by separating the reactants by gel permeation chromatography by HPLC. This technique separates the daunorubicin/SEQ ID NO:54 conjugates from free daunorubicin, free ST peptide, drug-drug conjugates and ST peptide-ST peptide conjugates. Homogeneous preparations of SEQ ID NO:54-daunorubicin conjugates coupled through their free amino groups and with a preferred molar ST preserves receptor binding function. ratio of 1:1 are obtained. Complexing the free amino group of

I claim:

1. A method of radioimaging metastasized colorectal cancer cells comprising the step of parenterally administering to an individual a pharmaceutical composition comprising:
    a) an pharmaceutically acceptable carrier or diluent, and,
    b) conjugated compound comprising:
        i) a ST receptor binding moiety; and,
        ii) an active moiety;
        wherein said pharmaceutical composition is sterile, said active moiety is a radioactive agent and said conjugated compound is present in an amount effective for diagnostic use in a humans suffering from colorectal cancer; wherein the localization and accumulation of said conjugated compound in the human body may be detected.

2. The method of claim 1 wherein said pharmaceutical composition is administered for delivery into said individuals circulatory system.

3. An in vitro method of screening an individual for metastasized colorectal cancer comprising the step of analyzing a sample of extraintestinal tissue or body fluid from an individual to detect ST receptor protein or mRNA encoding ST receptor protein in said sample wherein the presence of ST receptor or mRNA encoding ST receptor protein is indicative of metastasized colorectal cancer.

4. The method of claim 3 wherein said ST receptor protein or said mRNA encoding ST receptor protein is detected by the assay selected from the group consisting of: immunoassay to detect ST receptor protein wherein said sample is contacted with detectable antibodies that specifically bind to ST receptor; ST receptor binding assay to detect ST receptor protein wherein said sample is contacted with labelled ST receptor ligand; polymerase chain reaction to detect mRNA encoding ST receptor protein wherein said sample is contacted with primers that selectively amplify mRNA or cDNA that encodes ST receptor protein.

5. An in vitro method of determining whether a tumor cell is a colorectal tumor cell comprising the step of determining whether said tumor cell expresses ST receptor protein, wherein expression of ST receptor protein by said tumor cell indicates that said tumor cell is a colorectal tumor cell; wherein expression of said ST receptor protein by said tumor cell is determined by an assay selected from the group consisting of: an immunoassay wherein said tumor cell is contacted with detectable antibodies that specifically bind to ST receptor; an ST receptor binding assay wherein said tumor cell is contacted with labeled ST receptor ligand; and a polymerase chain reaction wherein said tumor cell is contacted with primers that selectively amplify mRNA or cDNA that encodes ST receptor protein.

6. A method of treating an individual suspected of suffering from metastasized colorectal cancer comprising the step of administering parenterally to said individual a therapeutically effective amount of a sterile pharmaceutical composition that comprises
   a) a pharmaceutically acceptable carrier or diluent, and,
   b) a conjugated compound which comprises
      i) a ST receptor binding moiety; and,
      ii) an active moiety that is a therapeutic agent that causes cell death;
      wherein said conjugated compound binds to an ST receptor on a metastasized colorectal tumor cell and said active moiety causes the death of said cell.

7. The method of claim 6 wherein said pharmaceutical composition is administered for delivery into said individuals circulatory system.

8. A method of treating an individual suspected of suffering from metastasized colorectal cancer comprising the step of administering parenterally to said individual for delivery into said individual's circulatory system a therapeutically effective amount of a pharmaceutical composition comprising:
   a) a pharmaceutically acceptable carrier or diluent, and,
   b) an amount of conjugated compound effective for therapeutic use in a human suffering from colorectal cancer, said conjugated compound comprising:
      i) an ST receptor binding moiety; and,
      ii) an active moiety;
   wherein said pharmaceutical composition is sterile and said active moiety is a radioactive agent; wherein said conjugated compound binds to ST receptors on a metastasized colorectal cancer cell and accumulates on said cell, and radiation emitted from accumulated conjugated compound on said cell causes the death of said cell.

9. A method of delivering a nucleic acid molecule to a cell that expresses ST receptors in an individual comprising the step of administering to said individual a pharmaceutical composition comprising:
   a) a pharmaceutically acceptable carrier or diluent, and,
   b) a composition comprising:
      i) a ST receptor ligand; and,
      ii) a nucleic acid molecule
   wherein said ST receptor ligand of said composition binds to an ST receptor on said cell and said nucleic acid molecule is delivered to said cell.

10. A kit for determining whether a sample contains a colorectal cancer cell comprising:
   a first container comprising antibodies that bind to ST receptor protein and a second container that comprises an isolated ST receptor protein; or
   a first container comprising a detectable ST receptor ligand and a second container that comprises an isolated ST receptor protein; or
   a first container comprising a set of PCR primers, wherein a PCR reaction using said set of primers that amplifies a DNA molecule from a substrate of mRNA that encodes ST receptor protein or a set of primers that amplifies a DNA molecule from a substrate of cDNA of mRNA that encodes ST receptor protein molecule and a second container comprising a DNA molecule equal in size to a DNA molecule that is amplified by PCR using said first PCR primer and said second PCR primer and said mRNA or said cDNA; or
   a first container comprising a nucleic acid molecule that comprises a sequence identical and/or complementary to mRNA or cDNA that encodes ST receptor protein and a second container that comprises a nucleic acid molecule that hybridizes to the nucleic acid molecule in said first container.

* * * * *

UNITED STATES PATENT AND TRADEMARK OFFICE
CERTIFICATE OF CORRECTION

PATENT NO.   : 6,060,037
DATED        : May 9, 2000
INVENTOR(S)  : Scott A. Waldman It is certified that error appears in the above-identified patent and that said Letters Patent is hereby corrected as shown below:

Column 20,
Line 30, "131I" should be -- $^{131}$I --.
Line 45, "131I" should be -- $^{-131}$I --.

Column 21,
Line 7, "131I" should be -- -$^{131}$I --.
Line 10, "$^{131}$-ST" should be -- $^{131}$I - ST --.

Column 23,
Line 37, "131Cs" should be -- $^{131}$Cs --.
Line 38, "1910s" should be -- $^{191}$Os --.

Column 42,
Line 19; after "No. The number "30" should not be there.

Signed and Sealed this

Second Day of October, 2001

Attest:

*Nicholas P. Godici*

NICHOLAS P. GODICI
*Attesting Officer*   *Acting Director of the United States Patent and Trademark Office*